(12) United States Patent
Davis et al.

(10) Patent No.: US 10,888,393 B2
(45) Date of Patent: *Jan. 12, 2021

(54) CLEANING DEVICE AND METHOD FOR FLUID TRANSFER CONNECTOR

(71) Applicant: NEOMED, INC., Woodstock, GA (US)

(72) Inventors: Benjamin M. Davis, Woodstock, GA (US); Aaron N. Ingram, Canton, GA (US)

(73) Assignee: NeoMed, Inc., Woodstock, GA (US)

( * ) Notice: Subject to any disclaimer, the term of this patent is extended or adjusted under 35 U.S.C. 154(b) by 178 days.

This patent is subject to a terminal disclaimer.

(21) Appl. No.: 15/938,607

(22) Filed: Mar. 28, 2018

(65) Prior Publication Data

US 2018/0214242 A1    Aug. 2, 2018

Related U.S. Application Data

(63) Continuation of application No. 15/009,073, filed on Jan. 28, 2016, now Pat. No. 9,931,176.

(Continued)

(51) Int. Cl.
*A61B 90/70* (2016.01)
*B08B 1/00* (2006.01)
(Continued)

(52) U.S. Cl.
CPC ........... *A61B 90/70* (2016.02); *A46B 9/02* (2013.01); *A61J 15/0026* (2013.01);
(Continued)

(58) Field of Classification Search
CPC ........... A61B 90/70; A61B 2090/701; A61J 15/0026; A61M 2209/10; A61M 39/16; A61M 39/20; A61L 2202/10; A61L 2202/17; A61L 2202/20; A61L 2202/24; A61L 2/00; A61L 2/02; A61L 2/16;
(Continued)

(56) References Cited

U.S. PATENT DOCUMENTS

| 1,523,754 A | 1/1925 | Chippeaux |
| 1,710,127 A | 4/1929 | Vaughn |

(Continued)

FOREIGN PATENT DOCUMENTS

| DE | 202009009091 U1 | 9/2009 |
| JP | 2001309973 A | 4/2003 |

OTHER PUBLICATIONS

Capture of youtube video of use of EnClean brush having a date of Sep. 11, 2015. (Year: 2015).*

(Continued)

*Primary Examiner* — Mark Spisich
(74) *Attorney, Agent, or Firm* — Dority & Manning, P.A.

(57) ABSTRACT

A cleaning swab device and method for cleaning a fluid coupling or connector. The device includes a generally elongate cylindrical tubular swab body, and a channel formed at an end thereof to define at least one cleaning finger for insertion into a housing and/or port of the connector to remove residual fluids, clean and disinfect the connector. The cleaning device optionally further includes a guide stem or plunger configured to extend through the tubular body of the swab, having a plug at one end for sealing debris out of a lumen of the connector during cleaning.

23 Claims, 15 Drawing Sheets

Related U.S. Application Data

(60) Provisional application No. 62/108,824, filed on Jan. 28, 2015.

(51) Int. Cl.
  *A46B 9/02* (2006.01)
  *B08B 9/027* (2006.01)
  *A61J 15/00* (2006.01)
  *A61M 5/00* (2006.01)
  *A61M 39/16* (2006.01)

(52) U.S. Cl.
  CPC .............. *B08B 1/002* (2013.01); *B08B 1/003* (2013.01); *B08B 1/006* (2013.01); *B08B 9/027* (2013.01); *A46B 2200/3006* (2013.01); *A46B 2200/3013* (2013.01); *A46B 2200/3073* (2013.01); *A61L 2202/17* (2013.01); *A61L 2202/24* (2013.01); *A61M 5/001* (2013.01); *A61M 39/16* (2013.01); *A61M 2209/10* (2013.01)

(58) Field of Classification Search
  CPC ..... A61L 2/18; A61L 2/26; A46B 9/00; A46B 9/02; A46B 9/005; A46B 15/00; A46B 2200/30; A46B 2200/3073; A46B 2200/3006; A46B 2200/3013; B08B 1/00; B08B 1/001; B08B 1/002; B08B 1/003; B08B 1/006; B08B 2240/00; B08B 9/00; B08B 9/02; B08B 9/021; B08B 9/023; B08B 9/027
  See application file for complete search history.

(56) References Cited

U.S. PATENT DOCUMENTS

| | | |
|---|---|---|
| 1,759,739 A | 5/1930 | Ferris |
| 2,190,216 A | 2/1940 | Nunziato |
| 2,629,888 A | 3/1953 | Sauer |
| 2,893,029 A | 7/1959 | Vosbikian et al. |
| 3,231,921 A | 2/1966 | Cuervo |
| 3,317,944 A | 5/1967 | Napier, Sr. et al. |
| 4,575,892 A | 3/1986 | Ross |
| 5,123,763 A | 6/1992 | Simmons |
| 5,214,820 A | 6/1993 | Shumway et al. |
| 5,222,271 A | 6/1993 | Eganhouse |
| 5,564,149 A | 10/1996 | Matesic et al. |
| 6,202,247 B1 | 3/2001 | Lorenz, Jr. |
| 6,250,315 B1 | 6/2001 | Ernster |
| 6,349,443 B1 | 2/2002 | Randolph et al. |
| 6,363,948 B2 | 4/2002 | Choi |
| 6,754,932 B2 | 6/2004 | Buzard |
| 6,935,802 B1 | 8/2005 | Byun |
| 7,198,611 B2 | 4/2007 | Connell et al. |
| 7,234,474 B2 | 6/2007 | Byun |
| 7,526,830 B2 | 5/2009 | Forrest et al. |
| 7,543,348 B2 | 6/2009 | Le |
| 7,763,013 B2 | 7/2010 | Baldwin et al. |
| 8,061,518 B2 | 11/2011 | Shaughness |
| 8,065,773 B2 | 11/2011 | Vaillancourt et al. |
| 8,079,106 B2 | 12/2011 | Yang |
| 8,172,825 B2 | 5/2012 | Solomon et al. |
| 8,197,749 B2 | 6/2012 | Howlett et al. |
| 8,214,961 B2 | 7/2012 | Vinci et al. |
| 8,252,247 B2 | 8/2012 | Ferlic |
| 8,336,151 B2 | 12/2012 | Kerr et al. |
| 8,336,152 B2 | 12/2012 | Vaillancourt et al. |
| 8,388,894 B2 | 3/2013 | Colantonio et al. |
| 8,407,846 B2 | 4/2013 | Chen et al. |
| 8,443,480 B2 | 5/2013 | Zaytoun, Jr. |
| 8,528,147 B2 | 9/2013 | Larsson et al. |
| 8,740,864 B2 | 6/2014 | Hoang et al. |
| 8,777,504 B2 | 7/2014 | Shaw et al. |
| 8,808,637 B2 | 8/2014 | Ferlic |
| 8,832,894 B2 | 9/2014 | Rogers et al. |
| 9,167,891 B2 | 10/2015 | Shaughness |
| 9,931,176 B2 | 4/2018 | Davis et al. |
| 2008/0052845 A1 | 3/2008 | Djang |
| 2008/0295281 A1 | 12/2008 | Kumaran |
| 2010/0050358 A1 | 3/2010 | Kim |
| 2010/0200017 A1 | 8/2010 | Kerr et al. |
| 2011/0314619 A1 | 12/2011 | Schweikert |
| 2012/0024734 A1 | 2/2012 | Shaughness |
| 2012/0124758 A1 | 5/2012 | Sabisch et al. |
| 2012/0186032 A1 | 7/2012 | Donohue et al. |
| 2013/0197485 A1 | 8/2013 | Gardner et al. |
| 2014/0261558 A1 | 9/2014 | Rogers et al. |
| 2015/0217106 A1 | 8/2015 | Banik et al. |
| 2016/0007729 A1 | 1/2016 | Kirkconnell-Shaughness |
| 2017/0042637 A1* | 2/2017 | Reinard ................ A61M 39/16 |

OTHER PUBLICATIONS

Bard Site-Scrub; 1 pg; date unknown.
EnClean Brush; 1 pg; date unknown.
New ISO Tubing Connector Standards: A Follow-Up to the Sentinel Event Alert Webinar PowerPoint Presentation; www.jointcommission.org; 50 pgs; Dec. 3, 2014.
New Tube Feeding Connectors Webinar PowerPoint Presentation; www.oley.org; 24 pgs; Jun. 24, 2014.

* cited by examiner

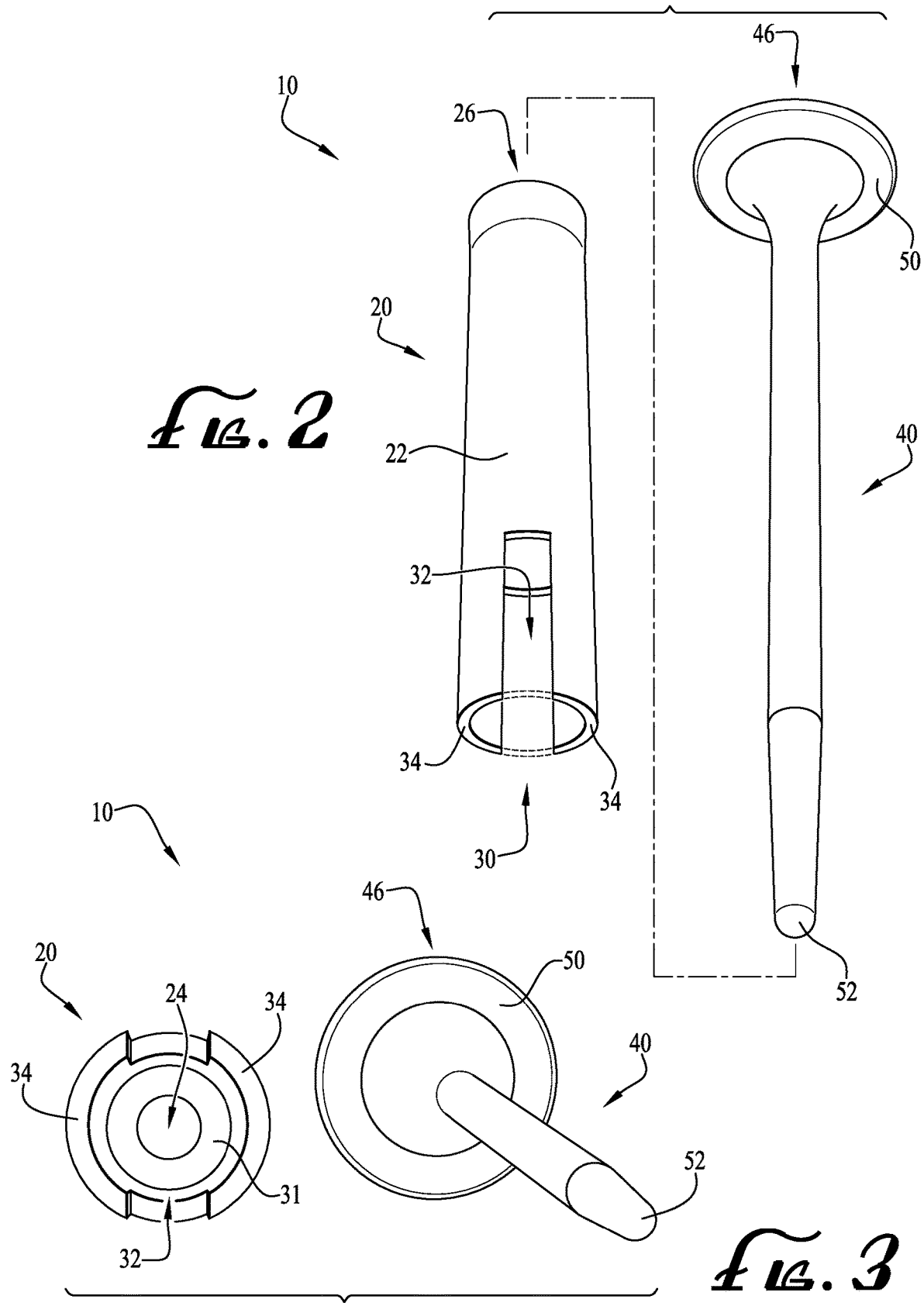

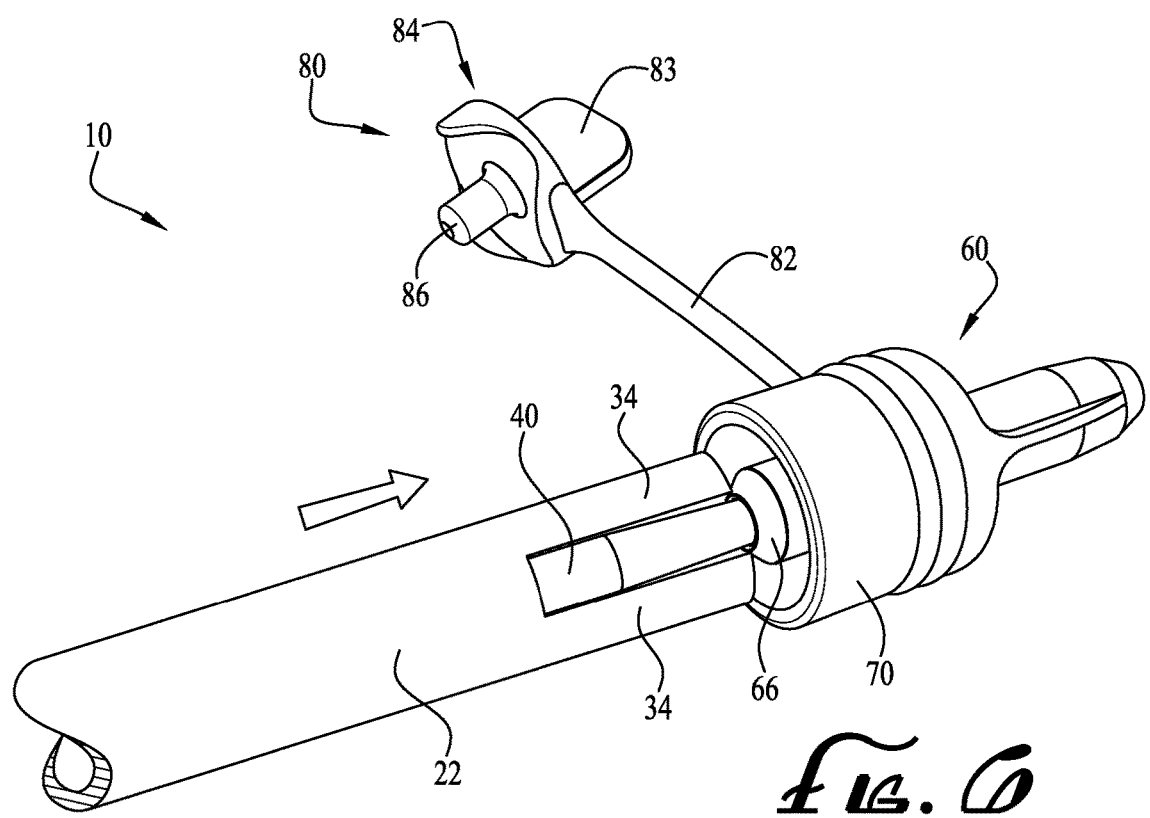
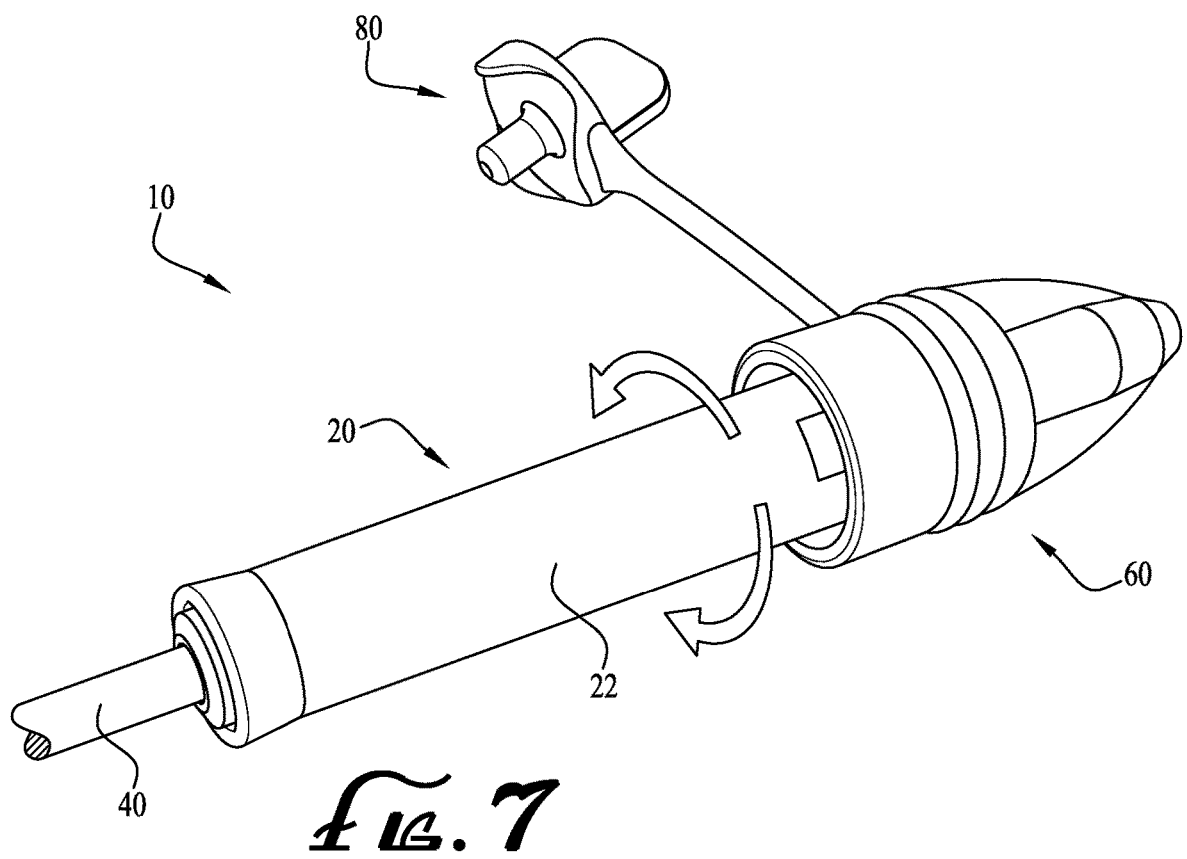

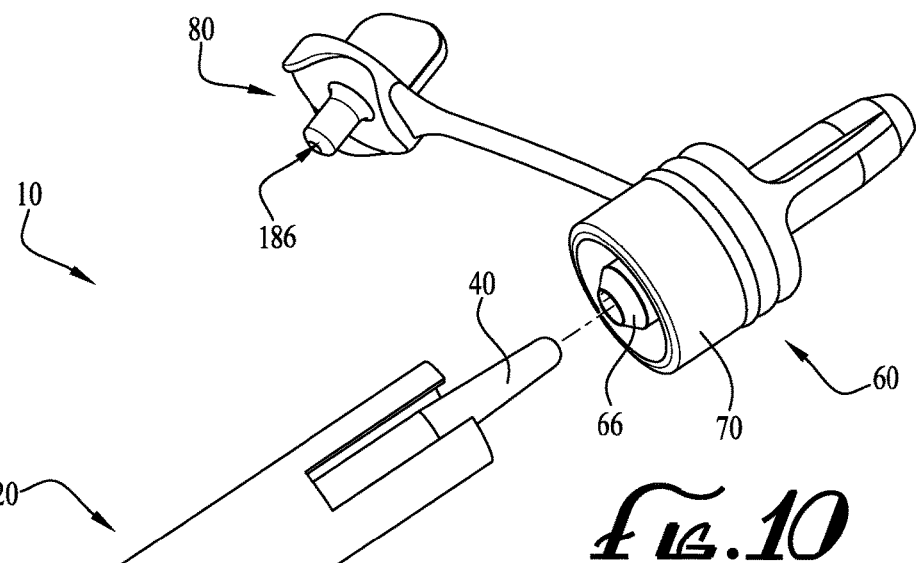
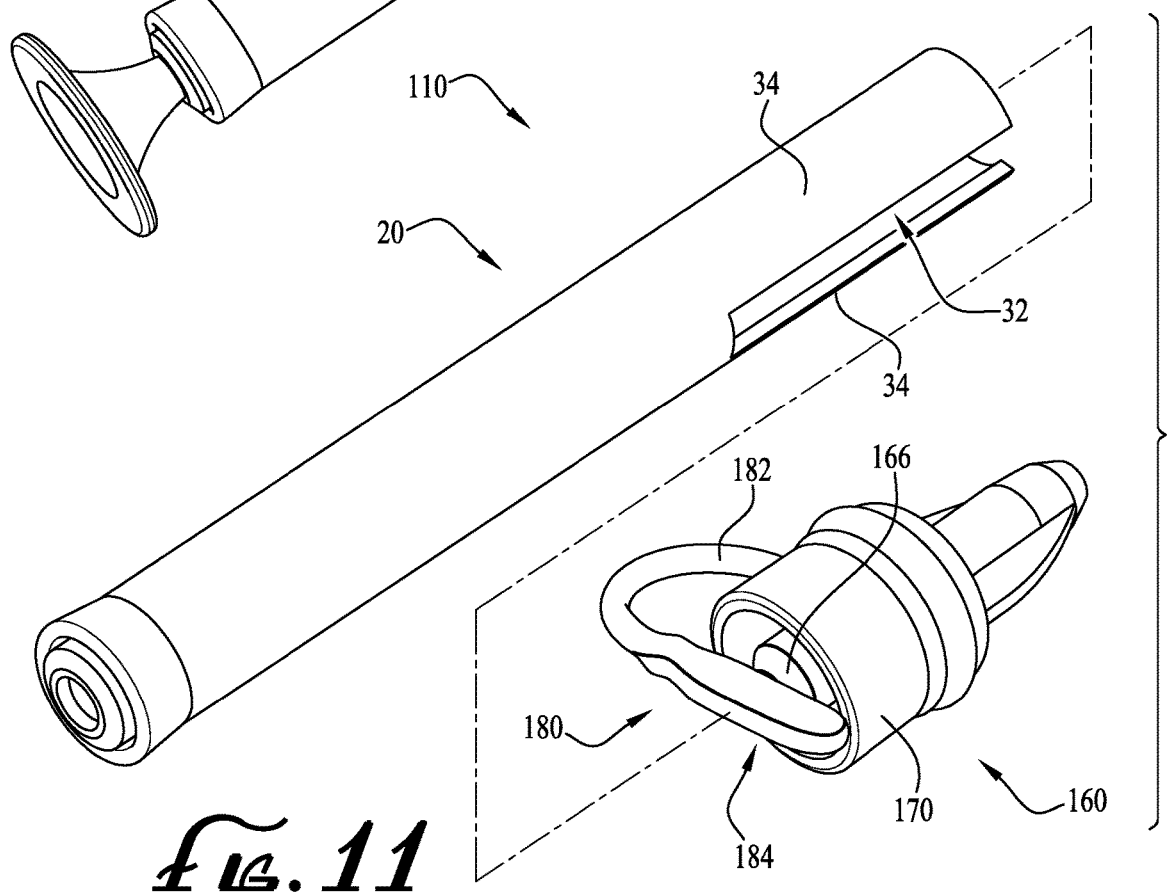

CLEANING DEVICE AND METHOD FOR FLUID TRANSFER CONNECTOR

CROSS-REFERENCE TO RELATED APPLICATIONS

This application is a continuation of U.S. Non-Provisional patent application Ser. No. 15/009,073 filed Jan. 28, 2016, now U.S. Pat. No. 9,931,176, which claims the priority benefit of U.S. Provisional Patent Application Ser. No. 62/108,824 filed Jan. 28, 2015, which is hereby incorporated by reference herein.

TECHNICAL FIELD

The present invention relates generally to the field of medical devices, and more particularly to cleaning devices and methods for use with fluid transfer connectors such as coupling connectors for enteral fluid containers.

BACKGROUND

Neonates and other healthcare patients are often administered fluids such as medications, nutritional fluids and supplements via enteral fluid delivery, commonly utilizing delivery systems including fluid containers, syringes, feeding tubes and other components. These components are often interconnected by connectors or couplings such as Luer connectors, or the more recently developed ENFit connector (ISO Standard 80369).

In some embodiments, these enteral connectors or couplings may include outer housing geometries with recesses or areas that could retain small quantities of unused feeding fluids that might allow for bacteria colonization or contain other potential contaminants. U.S. patent application Ser. No. 14/844,956, which is incorporated herein by reference, discloses a vented male ENFit enteral coupling or connector having a housing structure with drainage passages or vents to eliminate or reduce the likelihood of retaining feeding liquids or other contaminants in the outer housing. Further improvements in the field are desirable, and it is to the provision of cleaning swab devices and methods for enteral couplings or connectors that the present invention is primarily directed.

SUMMARY

In example embodiments, the present invention provides cleaning swab devices and methods for cleaning and/or disinfecting fluid transfer connectors or couplings, such as for example enteral feeding couplings. In example forms, the cleaning devices and methods are adapted for application with ENFit fluid transfer connectors in the form of male ENFit connectors, but the devices and methods of the present invention may likewise be adapted to use with other connectors or coupling formats.

In one aspect, the present invention relates to a cleaning device for cleaning a connector, the cleaning device including a generally elongate cylindrical swab member having a first end and a second end, the first end generally opposite the second end, an opening defined within the cylindrical member and extending from the first end to the second end, and a channel formed within a portion of the cylindrical swab member to define at least one finger, the at least one finger preferably comprising a cleaning material to provide for cleaning and/or disinfecting at least a portion of the connector.

In example embodiments, the at least one finger includes an interior surface, an exterior surface, an intermediate surface, and an end surface. In one example embodiment, at least a portion of one or more of the surfaces are at least partially covered with a cleaning material to provide for cleaning and disinfecting at least portions of the connector. According to example embodiments, the cleaning material is coated with a cleaning agent in the form of isopropyl alcohol, sterile water, saline, soapy water, or other agent.

In another aspect, the invention relates to a cleaning device for cleaning near and within at least one vent of a vented connector including a generally elongate cylindrical swab member having a first end and a second end, the first end generally opposite the second end, an opening defined within the cylindrical swab member and extending from the first end to the second end, and a channel formed within a portion of the cylindrical swab member to define at least two fingers, the at least two fingers at least partially comprising a material to provide for cleaning and disinfecting at least a portion of the vented connector; and a plunger extending from a first end to a second end, the plunger extending through the opening and comprising an actuating end at the first end and a plug end at the second end.

In example embodiments, the at least two fingers comprise interior surfaces, exterior surfaces, intermediate surfaces, and end surfaces. In one example embodiment, at least a portion of one or more of the surfaces are at least partially covered with a cleaning material to provide for cleaning and disinfecting at least portions of the vented connector. In another example embodiment, the cleaning material is coated with a cleaning agent in the form of isopropyl alcohol, sterile water, saline, soapy water, or other agent.

In still another aspect, the invention relates to a cleaning device for cleaning and/or disinfecting a connector, the connector including a stem having a lumen extending therethrough, an outer housing, and threads positioned on an internal portion of the outer housing, the cleaning device including a generally elongate tube extending from a first end to a second end and including an opening axially extending therethrough, wherein at least one end of the cleaning device can be inserted between the stem and the threads of the outer housing to clean and disinfect the connector.

In example embodiments, at least one end of the generally elongate tube includes a channel formed with a portion thereof to define at least one cleaning finger. The at least one cleaning finger includes an interior surface, an exterior surface, an intermediate surface and an end surface. In one example embodiment, one or more of the surfaces are at least partially covered with a cleaning material to provide for cleaning and disinfecting at least portions of the connector.

In yet another aspect, the invention relates to a cleaning device for cleaning and/or disinfecting a connector, the connector including a stem having a lumen extending therethrough, an outer housing, threads positioned on an internal portion of the outer housing, the connector further including a cap having a generally rib-like body, a seal plug extending from the rib-like body, and a tether connecting the cap to the connector, the seal plug generally provided for sealingly engaging the lumen of the stem. The cleaning device includes a generally elongate tube extending from a first end to a second end and having an opening axially extending therethrough, the cleaning device further including a channel formed with a portion of the cylindrical member to define at least one finger, wherein the at least one finger of the cleaning device can be inserted between the stem and the threads of the outer housing to clean and disinfect the connector with or without the seal plug sealingly engaging the lumen of the stem.

In still another aspect, the invention relates to a method of cleaning and/or disinfecting a connector. The connector generally includes a stem having a lumen extending therethrough, an outer housing, and threads positioned on an internal portion of the outer housing. The method includes providing a cleaning device having a generally elongate cylindrical member including a first end and a second end, the first end generally opposite the second end, and an opening defined within the cylindrical member and extending from the first end to the second end; engaging an end of the cleaning device with the connector, the end of the cleaning device generally being positioned between the stem and the threads of the connector; translating and/or rotating the cleaning device relative to the connector while the end of the cleaning device is engaged with the connector; and disengaging the cleaning device from the connector.

In yet another aspect, the invention relates to a cleaning device for cleaning a connector. The cleaning device includes a generally elongate housing, at least one brush member, and a plunger movably mounted to the housing. The housing includes a central opening extending therethrough. The at least one brush member is generally mounted to the housing and is generally laterally offset from the central opening. In example forms, the housing is generally cylindrical in shape and comprises a pair of flanges formed at an end thereof. In example forms, a pair of diametrically opposed channels are defined between the flanges. According to one example form, the at least one brush is mounted to the housing and is recessed within an orifice defined by the flanges, and wherein the channels defined between the flanges allow for the application of a cleaning agent to the at least one brush when a portion of the plunger is engaged with a portion of the connector.

In still another aspect, the invention relates to a cleaning device for cleaning a connector. In example embodiments, the connector includes a stem and a lumen extending therethrough. In example embodiments, the cleaning device includes a handle defining a longitudinal central axis, at least one brush mounted to the handle, a plunger coupled to the handle and generally extending along the longitudinal central axis.

In example embodiments, the at least one brush is positioned generally parallel to and laterally offset from the longitudinal central axis. In example embodiments, an end of the plunger is configured for projecting beyond an end of the handle for engagement with the stem of the connector. In example embodiments, the plunger is configured for sealing engagement with the lumen of the stem. In example embodiments, the connector further includes an outer housing surrounding the stem and a space defined between the stem and outer housing, and wherein with the plunger sealingly engaged with the lumen the at least one brush can occupy at least a portion of the space to clean the space. In example embodiments, the plunger is sized and shaped for sealing engagement with a lumen of an ISO 80369-3 formatted connector. In example embodiments, the ISO 80369-3 formatted connector includes a male EN Fit connector. In example embodiments, at least two brushes are mounted to the handle. In example embodiments, the at least one brush and plunger are mounted to the handle to extend in a generally similar direction. In example embodiments, the plunger is configured for extending at least partially beyond an end of the at least one brush.

In yet another aspect, the invention relates to a cleaning device for cleaning and/or disinfecting a connector. The connector includes a stem having a lumen extending therethrough, an outer housing and threads positioned on an internal portion of the outer housing. The cleaning device includes a generally elongate handle extending from a first end to a second end along a longitudinal axis, and a plunger and at least one brush mounted to the elongate handle, wherein the at least one brush can be inserted between the stem and the threads of the outer housing to clean the connector.

In example embodiments, the at least one brush is inserted between the stem and the threads, the plunger sealingly engages with the lumen. In example embodiments, an end of the plunger is configured for extending at least partially beyond an end of the at least one brush. In example embodiments, the connector includes an ISO 80369-3 formatted connector. In example embodiments, the ISO 80369-3 formatted connector includes a male ENFit connector. In example embodiments, at least two brushes are mounted to the handle. In example embodiments, the at least one brush and plunger are mounted to the handle to extend in a generally similar direction.

In still another aspect, the invention relates to a cleaning device for cleaning a connector. The connector including a stem having a lumen extending therethrough. The cleaning device includes a handle configured to be gripped by a user for application of the cleaning device into operative engagement with the connector, a plunger coupled with the handle and configured for engagement with the lumen of the connector when the cleaning device is applied into operative engagement with the connector, and at least one brush coupled with the handle and laterally offset from the plunger, whereby the brush engages externally around the stem when the cleaning device is applied into operative engagement with the connector.

In example embodiments, the plunger is sized and shaped for sealing engagement with a lumen of an ISO 80369-3 formatted connector. In example embodiments, the ISO 80369-3 formatted connector includes a male ENFit connector. In example embodiments, an end of the plunger is configured for extending at least partially beyond an end of the at least one brush. In example embodiments, the at least one brush and plunger are coupled to the handle such that they extend in a generally similar direction. In example embodiments, at least two brushes are mounted to the handle.

These and other aspects, features and advantages of the invention will be understood with reference to the drawing figures and detailed description herein, and will be realized by means of the various elements and combinations particularly pointed out in the appended claims. It is to be understood that both the foregoing general description and the following brief description of the drawings and detailed description of the invention are exemplary and explanatory of example embodiments of the invention, and are not restrictive of the invention, as claimed.

BRIEF DESCRIPTION OF THE DRAWINGS

FIG. 2 shows a disassembled perspective view of the cleaning device of FIG. 1.

FIG. 3 shows a front perspective view of the cleaning device of FIG. 1.

FIGS. 6-10 show a sequence of operation using the cleaning device of FIG. 1 to clean a connector, according to an example method of the present invention.

FIG. 11 shows a cleaning device according to another example embodiment of the present invention, and a connector with which the cleaning device may be utilized.

DETAILED DESCRIPTION OF EXAMPLE EMBODIMENTS

Figure 1:
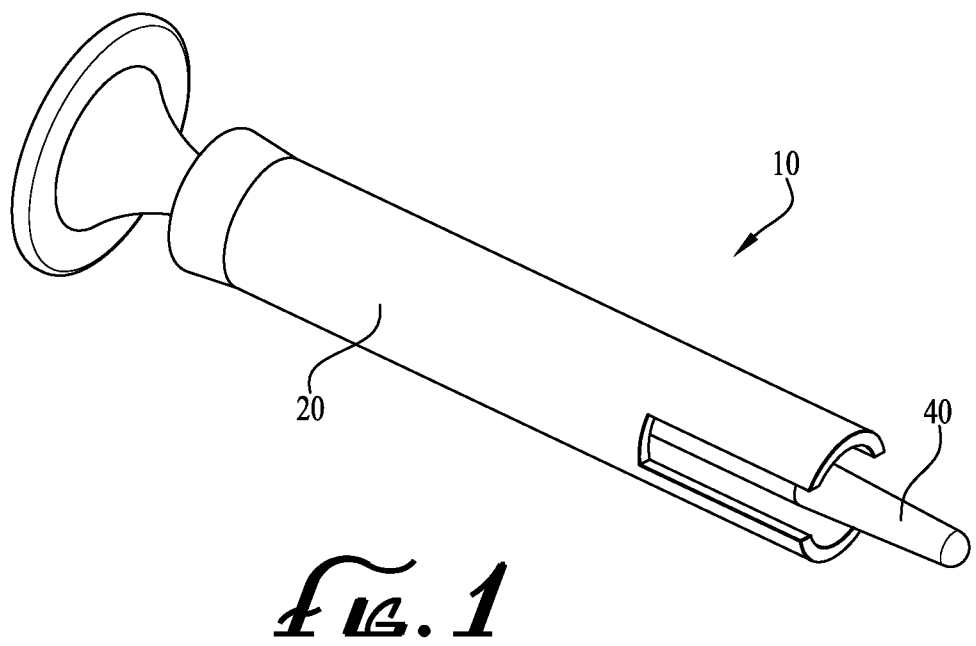
FIG. 1 shows a perspective view of an assembled cleaning device according to an example embodiment of the present invention.

The present invention may be understood more readily by reference to the following detailed description of the invention taken in connection with the accompanying drawing figures, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Any and all patents and other publications identified in this specification are incorporated by reference as though fully set forth herein.

Also, as used in the specification including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

With reference now to the drawing figures, wherein like reference numbers represent corresponding parts throughout the several views, example embodiments of the invention will be described. FIGS. 1-5 show a cleaning device or swab assembly 10 according to an example embodiment of the present invention. In this embodiment, the cleaning device 10 generally comprises a swab member 20 and a guide shaft or plunger 40. The swab 20 comprises an elongate cylindrical tube member or handle 22, and extends from a first end 26 to a second end 30. In example embodiments, an opening or lumen 24 extends through the swab 20 from the first end 26 to the second end 30. As depicted in FIG. 3, the first end of the swab 20 generally includes a wall or end portion 31 formed with the swab 20 and defines the opening 24 formed generally at a central portion thereof. The second end 30 of the swab 20 generally includes at least one elongate channel 32 (in the depicted embodiment, two diametrically opposed cutout portions of the tubular body of the swab 20 define the channel 32), forming a pair of projections or swab fingers 34 at the second end 30 of the swab 20, the projections 34 being configured to extend within an outer housing of a connector (and/or within and/or through drainage openings or vents of the connector) to clean and disinfect the connector whereby any residual feeding liquids or other debris retained within the connector is removed.

Figure 5:
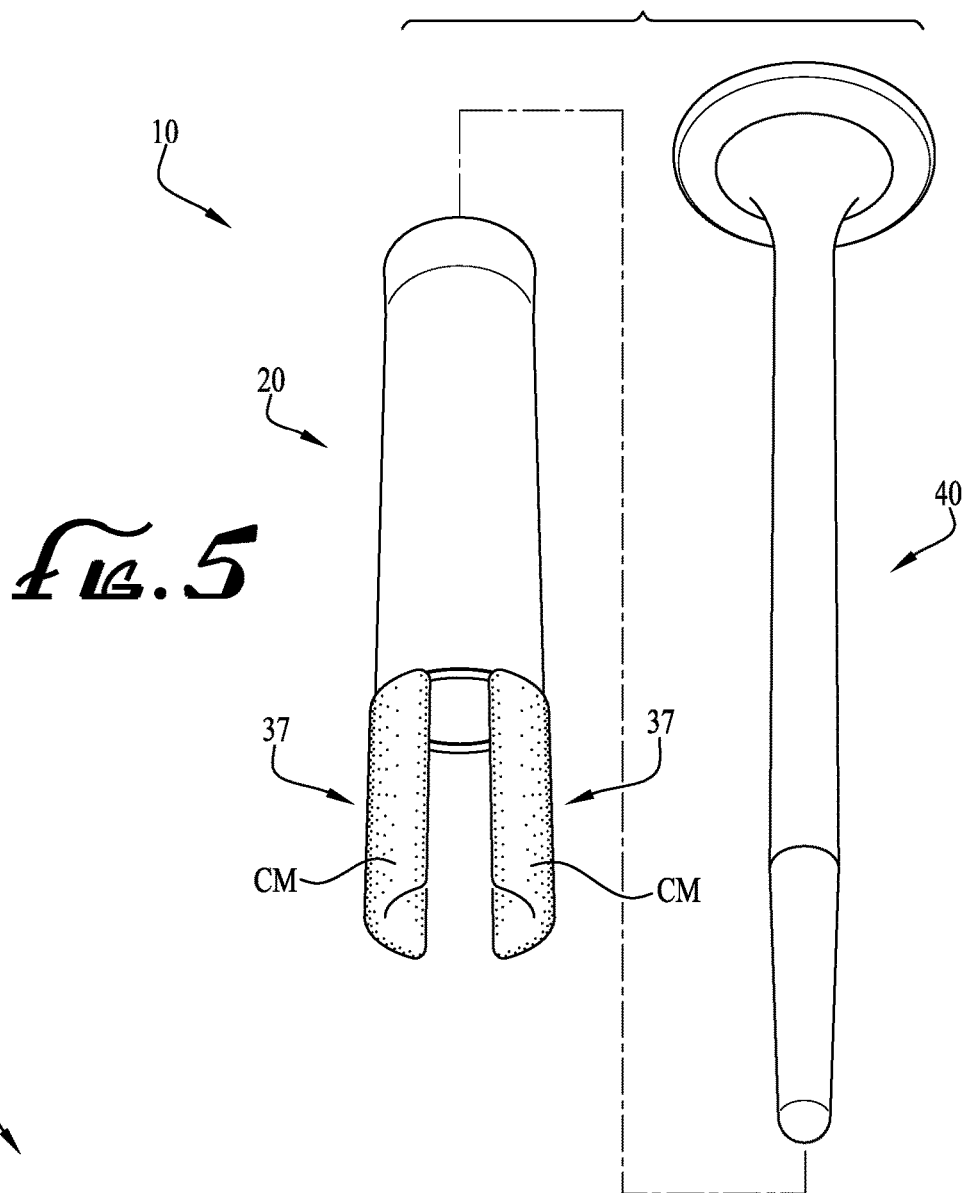
FIG. 5 shows the cleaning device of FIG. 1, indicating a tip portion thereof wherein foam or other cleaning material is applied.
Figure 4:
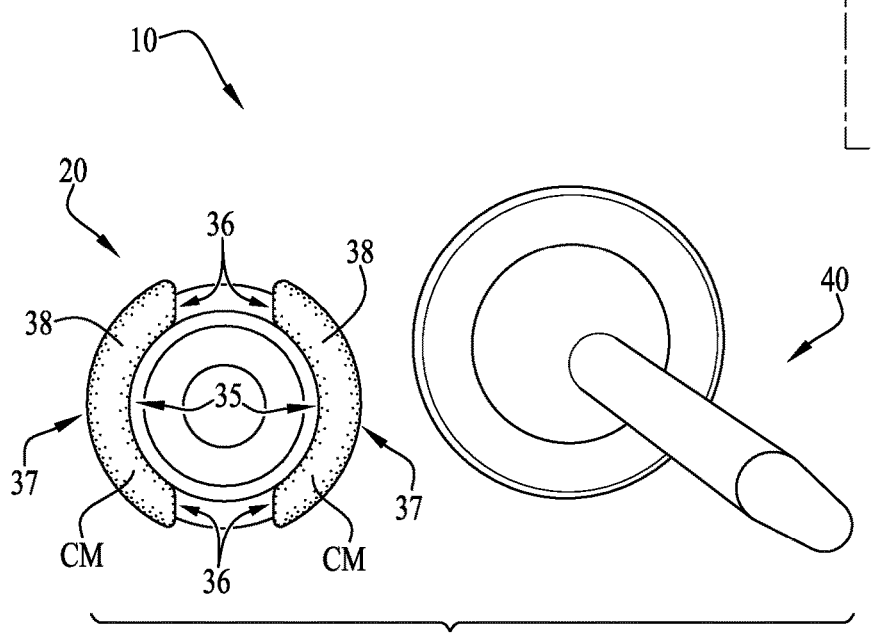
FIG. 4 shows the cleaning device of FIG. 1, showing a portion thereof defining an area wherein foam or other cleaning material is applied.

The projections 34 are shown in greater detail in FIGS. 4-5. In example forms, the projections 34 comprise interior surfaces 35, exterior surfaces 37, intermediate surfaces 36, and end surfaces 38. In example embodiments, at least a portion of one or more of the surfaces 35, 36, 37, 38 are at least partially covered with a foam material, flocking, or other cleaning material CM to provide for cleaning and disinfecting at least portions of the connector during its cycle of use. The foam material CM can optionally be coated with isopropyl alcohol (ISP) or other forms of antimicrobial, antibacterial or other disinfecting/cleaning agents. In example forms, the cleaning agent comprises 70% ISP. Alternatively, other cleaning agents such as sterile water, saline, soapy water, or other agents may be utilized. The foam or other cleaning material CM is preferably compressible, absorbent and textured to facilitate a scrubbing action against portions of the connector. According to some example forms, the cleaning material CM is in the form of a brush, for example, wherein a generally rigid wire comprising a plurality of bristles extending therefrom is provided for contacting and cleaning/disinfecting the connector (as will be described below).

Referring back to FIG. 2, the plunger 40 generally comprises a rod or shaft having an actuating or gripping portion such as a flange 50 formed at a first end thereof and a plug or tip portion 52 formed at a second end thereof. The actuating portion generally comprises a gripping pad or enlarged surface area 46 and the plug portion formed at the second end of the plunger 40 is configured for insertion and sealing within a lumen of the connector (as will be described below). In example embodiments, the flange 50 is sized to be larger than the opening 24 of the swab 20 to prevent the swab from being retracted over the flange and off of the plunger.

FIGS. 6-10 show a sequence of operation of the cleaning device used to clean a connector 60 according to an example method of use of the present invention. In the depicted embodiment, the connector 60 is generally in the form of the connector disclosed in U.S. patent application Ser. No. 14/844,956, which is incorporated herein by reference and shows an improved male ENFIT connector for enteral fluid containers and vessels that includes vent or drain openings to reduce the incidence of residual feeding liquids being retained within the outer housing 70 thereof where bacterial growth or contamination might occur. The connector 60 comprises a front end, the stem 66 (comprising a lumen extending therethrough), the outer housing 70, threads 372 positioned on an internal portion of the outer housing 70 (see FIG. 25A), a pair of vent openings 174 (see FIG. 12), a cap 80, a tether 82 attaching the cap 80 to the connector 60, a handle 83 for gripping the cap 80, a body 84, and a seal plug 86.

As shown in FIG. 6, the swab 20 is mounted over the plunger 40 with the plug end 52 of the plunger projecting outwardly from the second end 30 of the swab 20. The plug 52 is removably inserted into the lumen of the male connector stem 66 of the connector 60 to seal the lumen extending through the stem 66. According to example forms, the plug sealingly engaging the lumen preferably prevents contamination of the lumen from debris or the cleaning agent during the cleaning process (as will be described below). In example forms, a user's thumb or finger may press against the pad 46 and/or flange 50 to force the plug 52 to removably and sealingly engage the lumen. According to some example forms, the plug 52 is generally sized and shaped similarly to the seal plug 86 of the cap 80.

Figure 8:
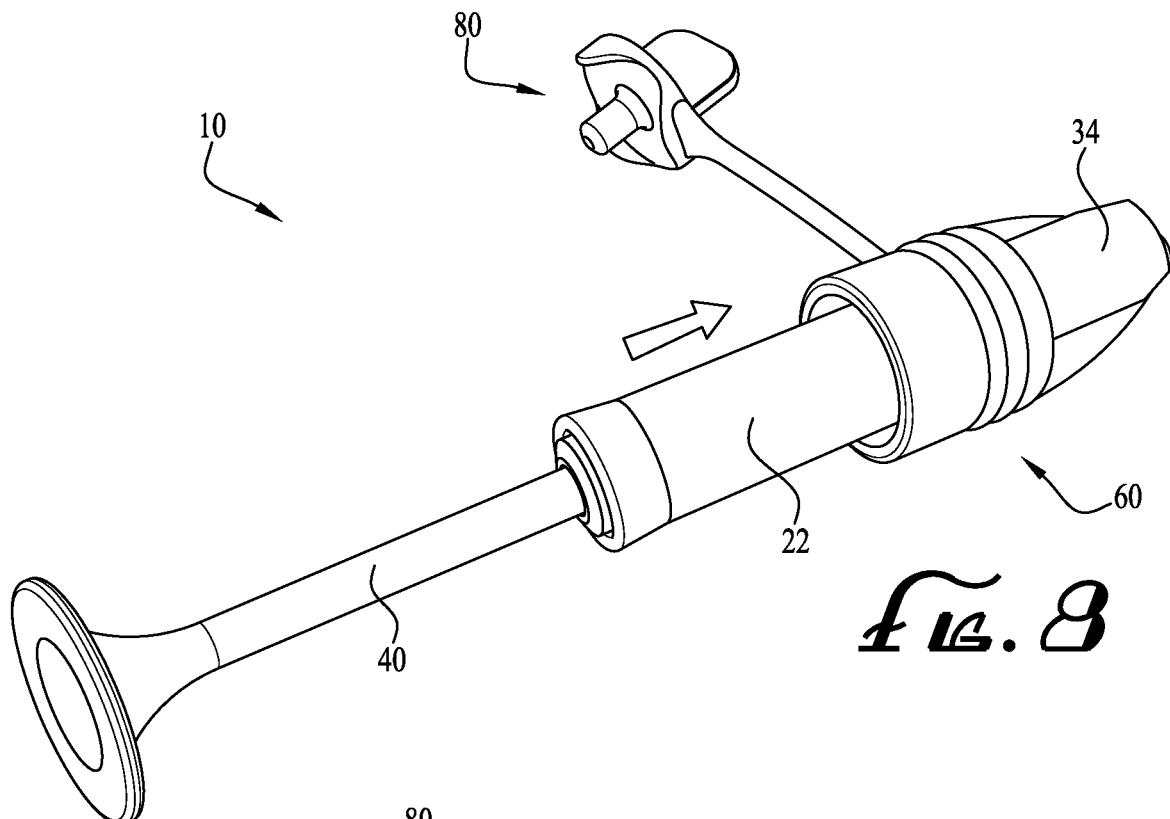

Once the plug is inserted and sealed within the lumen of the connector stem 66, the swab 20 is advanced in a traversing or translational movement along the plunger 40 such that the projections 34 begin to move between the outer housing 70 and the connector stem 66. As shown in FIG. 7, the projections 34 are generally positioned between the outer housing 70 and the stem 66 so that the swab 20 is capable of rotation about the plunger 40, thereby allowing the projections 34 to rotationally move therebetween to clean and/or disinfect (e.g., removing any feeding fluids or other debris and potential contaminants that may be contained therein). Next, as shown in FIG. 8, the swab 20 is further advanced along the plunger 40 such that the projections 34 extend through the vent openings 74 of the connector 60 to further clean and/or disinfect the connector and remove any feeding fluid or residue present due to fluid drainage through the vent openings 74. Thus, by having the plug sealingly engaged with the lumen of the stem 66, debris and/or the cleaning agent of the projections 34 (or foam material CM thereof) are prevented from being introduced into the lumen when cleaning (e.g., translational and/or rotational motion of the swab 20 whereby the projections 34 are generally positioned between the outer housing 70 and the connector stem 66).

Figure 9:
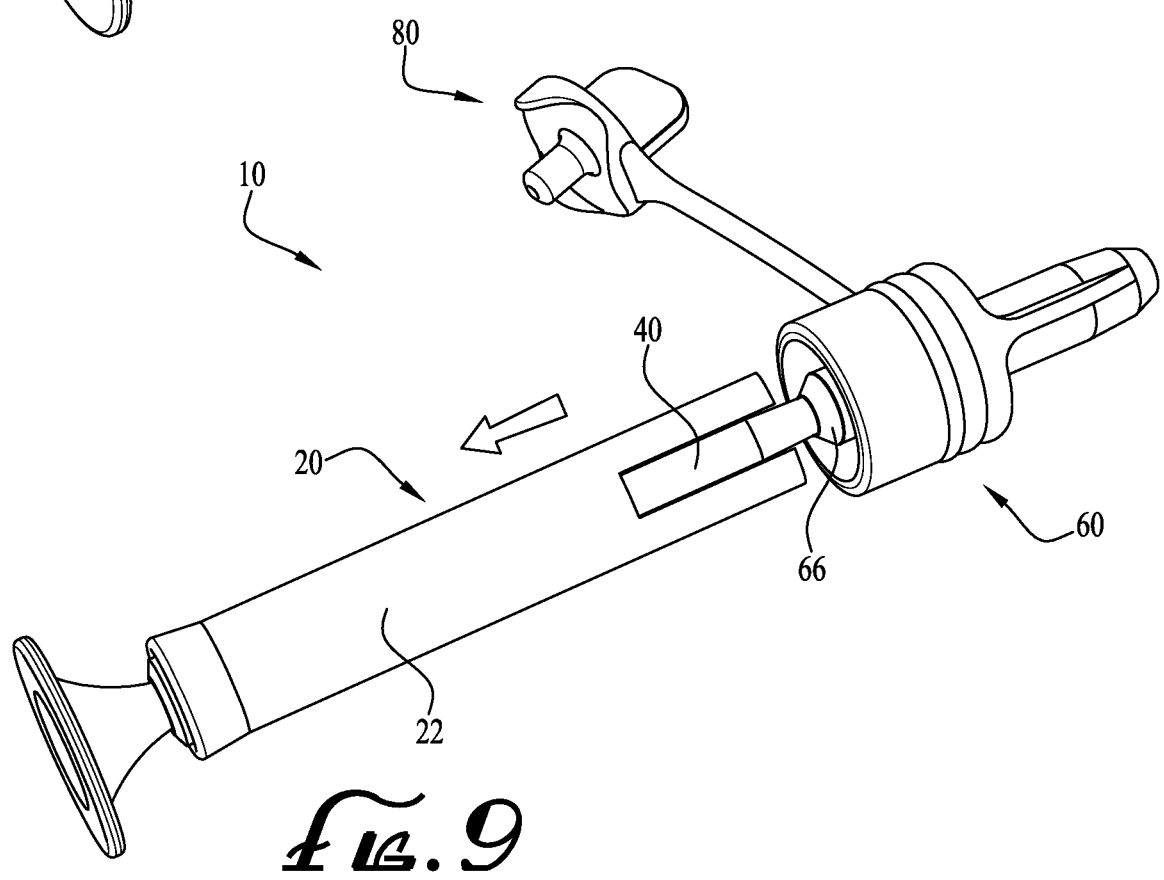

As shown in FIG. 9, the swab 20 can then be retracted rearward, causing the projections 34 to be withdrawn from the vent openings 74 and from between the stem 66 and outer housing 70. The plug end 52 of the plunger 40 preferably remains inserted in the lumen of the connector stem 66 while the swab 20 is withdrawn from the connector 60 to prevent contamination that may be present on the swab from entering the lumen of the connector stem. After the swab is withdrawn, the plug 52 is disengaged from the lumen of the connector stem 66 as shown in FIG. 10. In example forms, traversing the swab 20 along the plunger 40 is generally carried out by grasping a portion of the tube 22, and engaging and disengaging the plug 52 to/from the lumen of the connector stem 66 is carried out by pressing or pulling on the actuating end of the plunger 40 (e.g., the pad 46 and/or flange 50). After the plug 52 is disengaged from the lumen of the connector stem 66, the seal plug 86 of the cap 80 can then be inserted into the lumen of the connector stem 66 so that further contamination therein is prevented.

Optionally, according to additional example embodiments of the present invention, the channel 32 of the swab 20 can be configured to follow a generally helical path such that the pair of projections 34 generally follow a helical path, for example, instead of the projections 34 being generally linear as depicted. In this manner, the projections 34 can still be positioned between the outer housing 70 and the stem 66 so that the swab 20 is capable of rotation about the plunger 40, thereby allowing the projections 34 to rotationally move therebetween to clean and/or disinfect (e.g., removing any feeding fluids or other debris and potential contaminants that may be contained therein). Furthermore, when the swab 20 is further advanced along the plunger 40 such that the projections 34 extend through the vent openings 74, the swab 20 is rotated (and translated) to cause greater or less engagement with the vent openings 74, for example, since the channel 32 follows a helical path. Thus, in example forms, rotational movement can be provided for cleaning of the connector when the projections 34 are positioned between the outer housing 70 and the stem 66 and when the projections 34 move through the vent openings 74.

Figure 12:
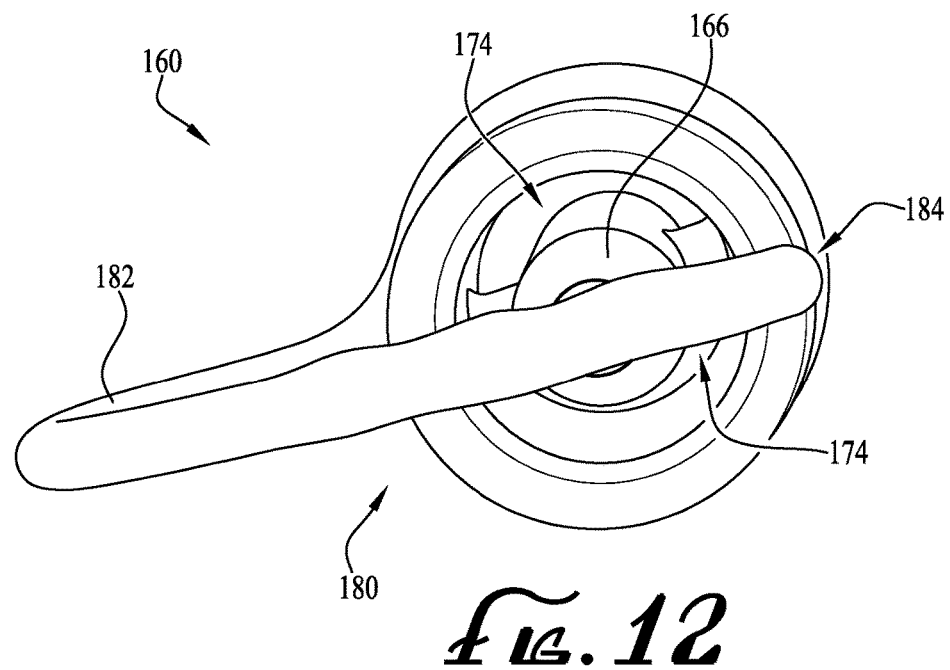
FIG. 12 shows an end view of the connector of FIG. 11.
Figure 13:
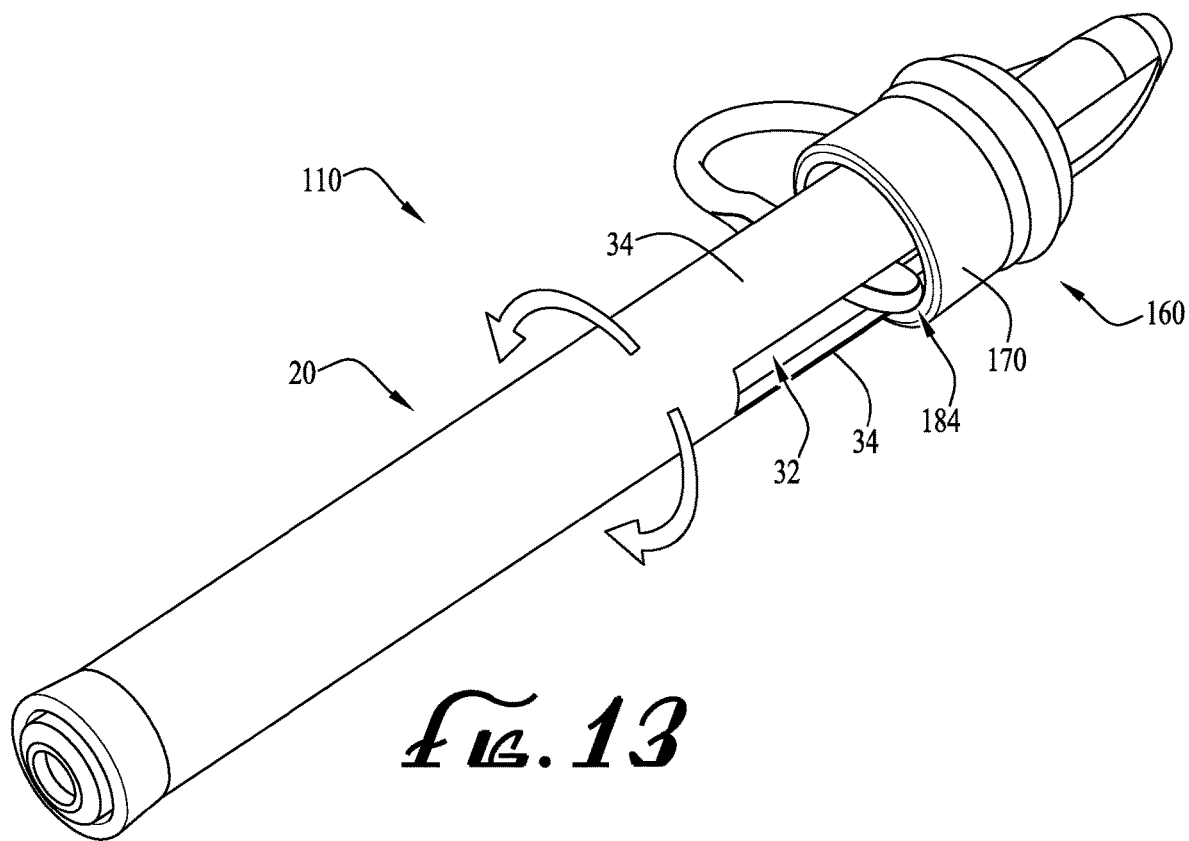
FIGS. 13-14 show a sequence of operation using the cleaning device of FIG. 11 to clean the connector, according to another example method of the present invention.
Figure 14:
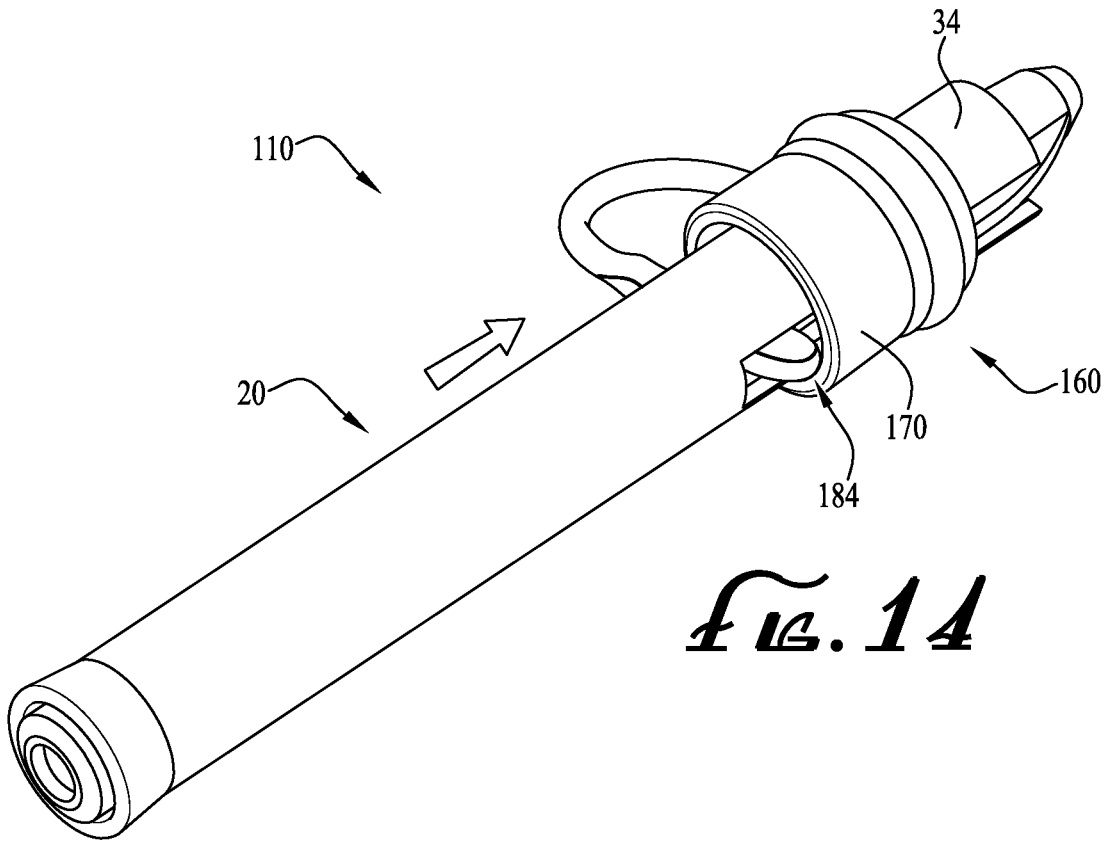

FIGS. 11-14 show a cleaning device or swab assembly 110 comprising a swab 20 substantially as described above, and a modified coupling or connector 160 according to another example embodiment of the present invention. The connector 160 comprises a cap 180 comprising a generally flanged or rib-like body 184 and a seal plug 186 extending therefrom (shown as being fully inserted within the lumen of the stem 166). In example embodiments, a tether 182 optionally connects the cap 180 to the connector 160, as similarly described above. Preferably, rather than providing a plunger for sealing the lumen of the connector stem 166, the seal plug 186 is utilized to seal the lumen while also allowing the projections 34 of the swab 20 to be inserted between the outer housing 170 and the stem 166. As depicted in FIG. 12, the rib-like body 184 of the cap 180 is preferably configured, sized and shaped to fit within the channel 32 of the swab 20 and to allow the projections 34 to extend within the connector, between the outer housing 170 and the stem 166 (see FIG. 13), and within and through the vent openings 174 (see FIG. 14). Preferably, as shown in FIG. 13, when the projections 34 are inserted within the connector 160 (between the outer housing 170 and the stem 166), the body 184 of the cap 180 is received within the channel 32. In an example manner of use, the seal plug 186 remains sealingly engaged with the lumen of the stem 166, and the swab 20 can be rotated to clean within the housing and vent openings, which causes the plug 180 and tether 182 to rotate therewith. As depicted in FIG. 14, the swab 20 can be further advanced within the connector 160 such that the projections 34 extend through the vent openings 174. In example forms, since the seal plug 186 is plugging the lumen rather than the plunger 40 as described above, the channel 32 of the swab may be sized accordingly (e.g., width, length, etc.) to provide for fitting around the body 184 and permitting adequate extension of the projections 34 through the vent openings 174.

Figure 15:
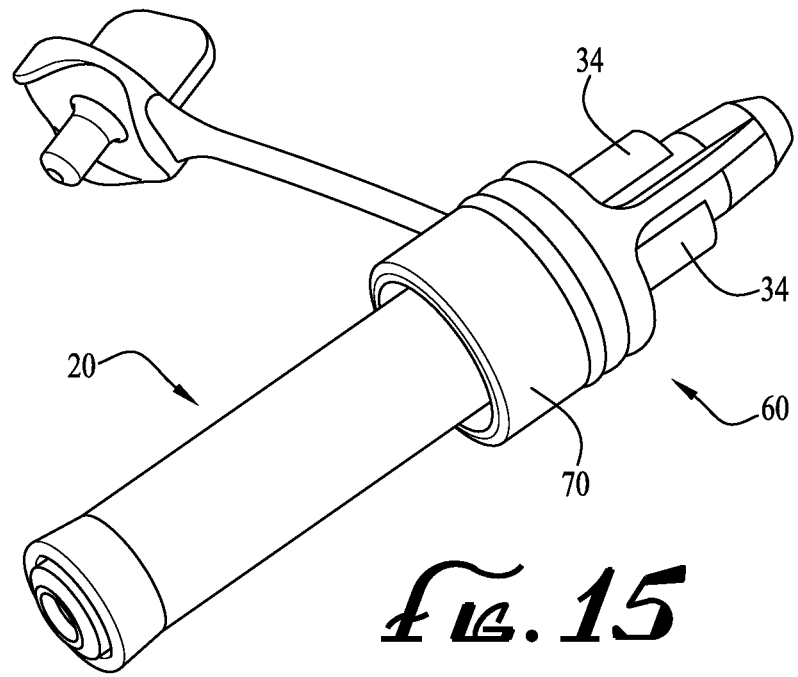
FIG. 15 shows a cleaning device engaged with a portion of a connector, according to another example embodiment of the present invention.

FIG. 15 shows another method of use of the swab 20 to clean a connector 60 according to the present invention. As depicted, the swab 20 is applied for cleaning the connector 60 without the use of the plunger 40 or seal plug 86 to seal the lumen of the connector stem 66, for example when the risk of debris entering the lumen of the connector stem is small or is not of concern (e.g., a final wipe-down to remove residual fluid after use of the connector is complete, prior to disposal).

FIGS. 16-22 show a cleaning device 210 according to another example embodiment of the present invention. As depicted, the cleaning device 210 generally comprises a housing 212, at least one brush member 230 mounted to the housing 212, and a guide shaft or plunger 240. According to one example form, the housing 212 comprises a first housing half or shell 214 and a second housing half or shell 216, wherein the housing shells 214, 216 are generally similarly sized and shaped about an axis of symmetry, and whereby one or more snap fittings, crush pins, connectors or other coupling features thereof provide for joining the two shells 214, 216 together to form the housing 212. According to example forms, the housing 212 is generally cylindrical in shape and comprises a first end having a generally recessed area for receiving a portion of the plunger 240 (as will be described below) and a second end comprising a pair of generally elongate and oppositely-positioned flanges 224 defining an enlarged orifice 221 within the housing 212. According to example forms, the plug 252 of the plunger 240 is configured to be engaged with the lumen of the connector to be cleaned, and the housing 212 and brushes 230 attached thereto are configured to move along the plunger 240 so that the brushes can move within the outer housing and along an exterior of the stem of the connector so that the brushes 230 are capable of rotation about the plunger 240, thereby allowing the brushes 230 to rotationally move therebetween (e.g., between an outer portion of the stem and against an interior wall of the outer housing of the connector) to clean and/or disinfect (e.g., removing any feeding fluids or other debris and potential contaminants that may be contained therein).

Figure 19:
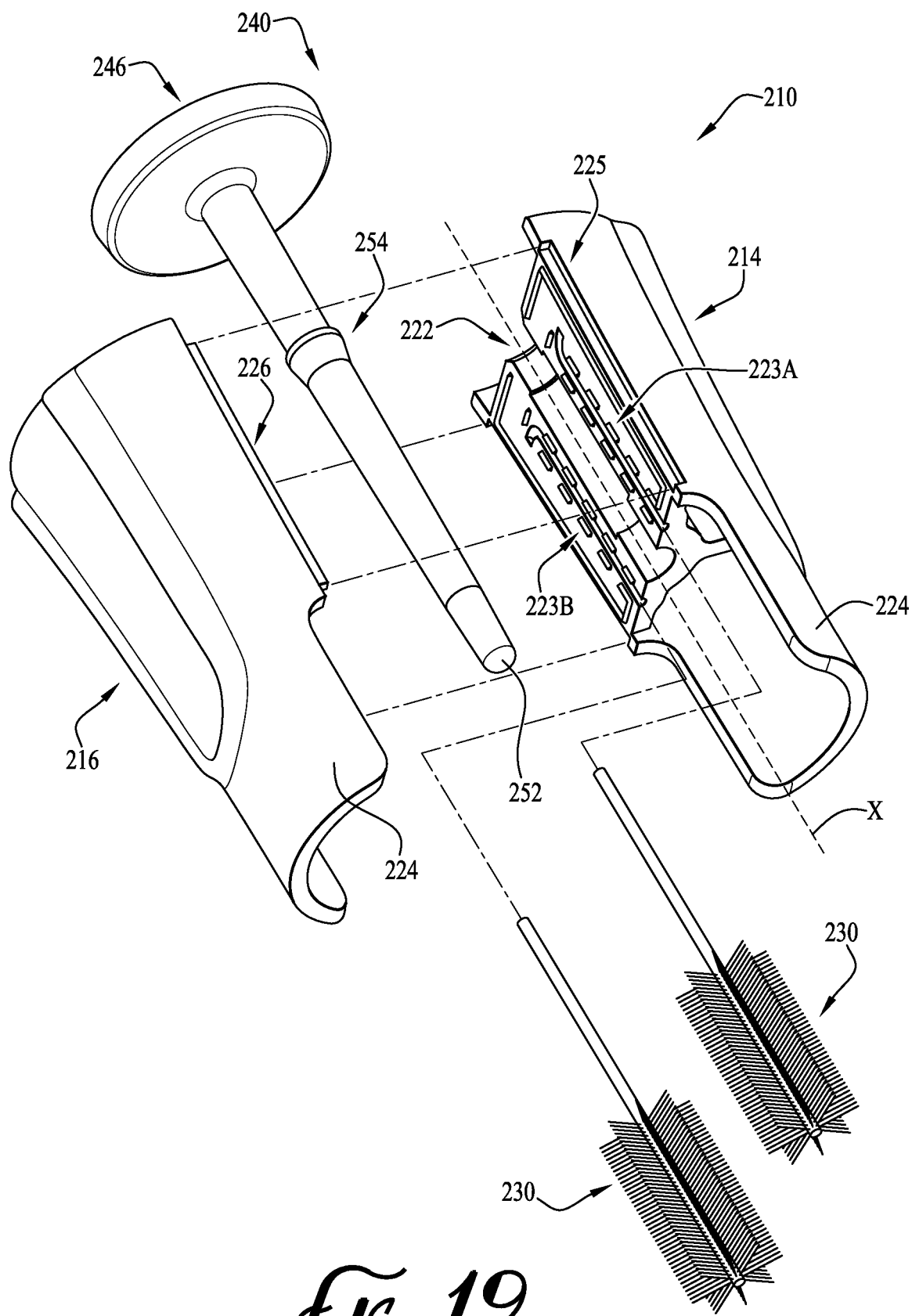
FIG. 19 shows a front perspective assembly view of the cleaning device of FIG. 16.
Figure 20:
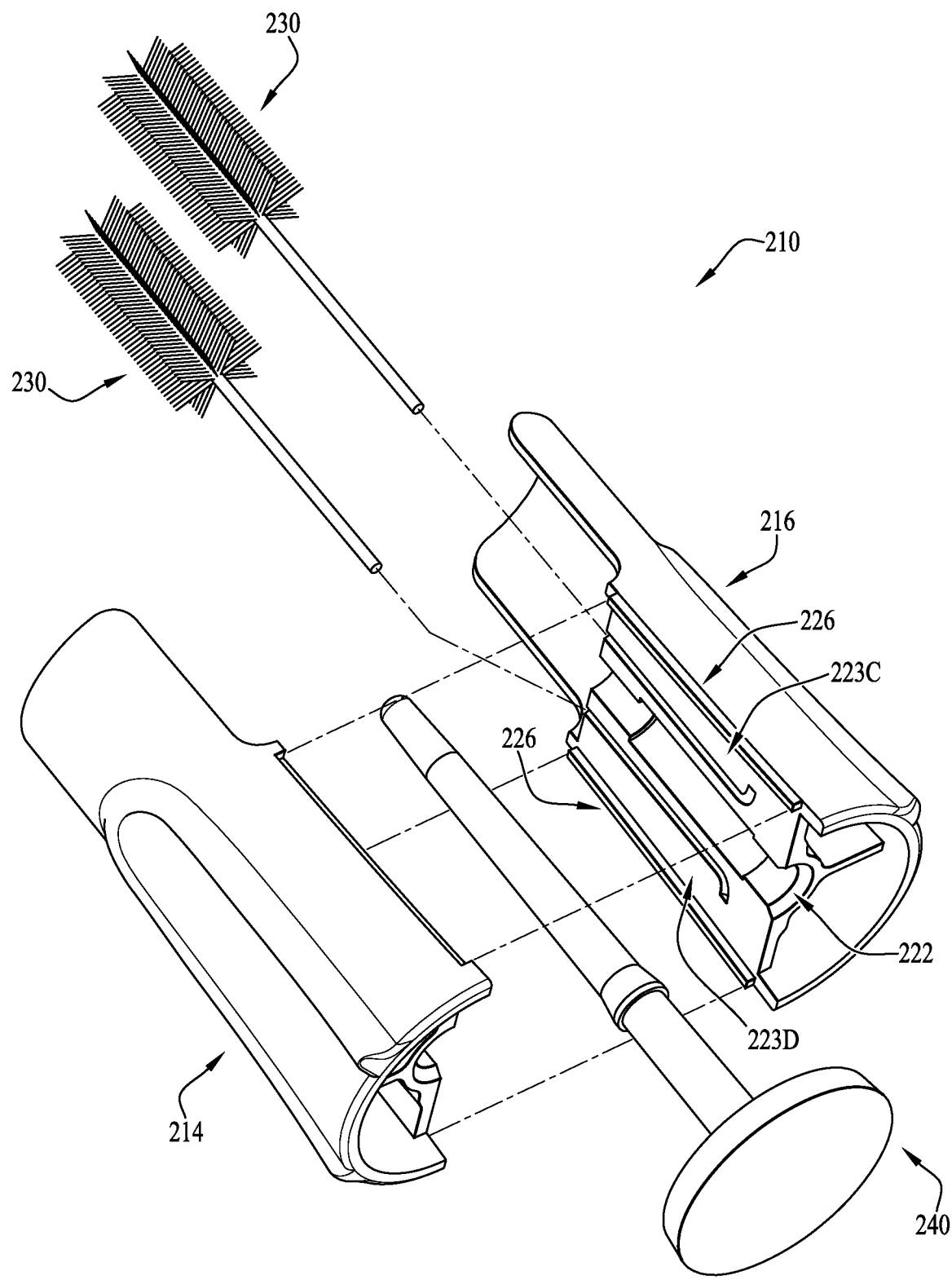
FIG. 20 shows a rear perspective assembly view of the cleaning device of FIG. 19.
Figure 24:
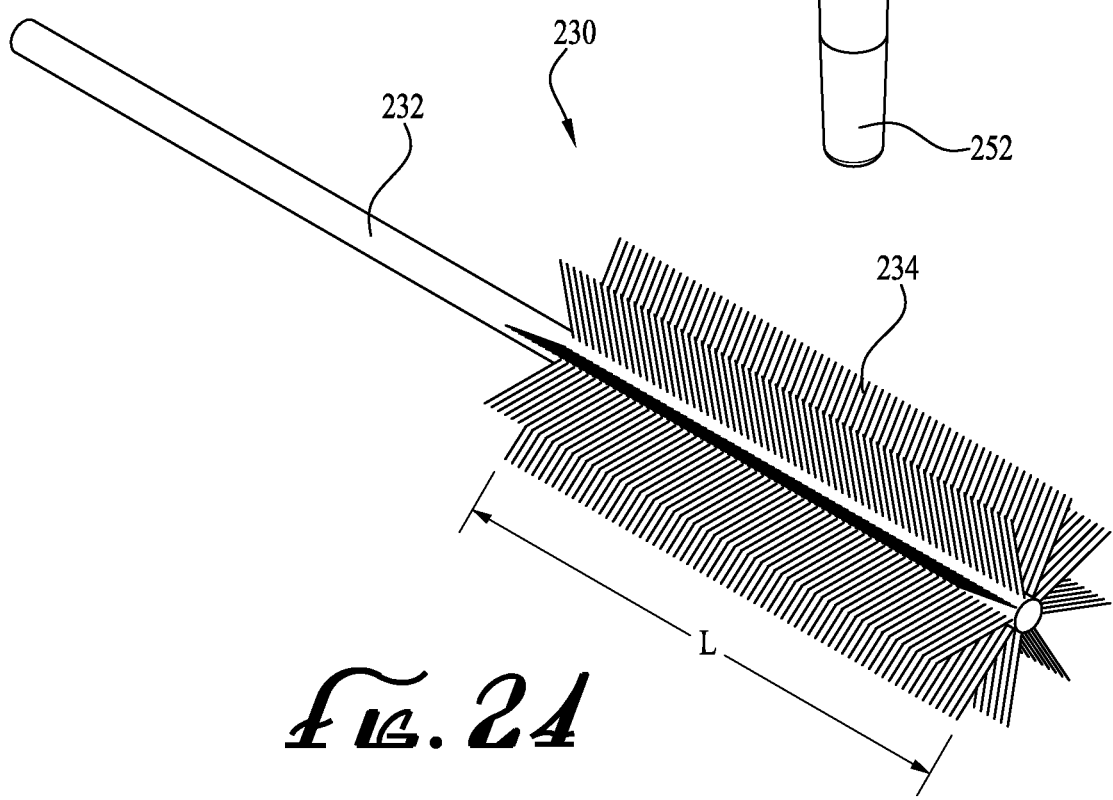
FIG. 24 shows a perspective view of a brush member of the cleaning device of FIG. 16.

As depicted in FIGS. 19-22, the shells 214, 216 comprise generally elongate channels 223A-D for receiving a rod portion 232 of the brushes 230 (see FIG. 24). According to example forms, the channels 223A-D are generally parallel and laterally offset a small distance from a central channel 222 defining a longitudinal central axis X that generally extends between the ends of the housing 212, for example, which provides for capturing a retaining feature 254 of the plunger 240, for example, to permit translation of the plunger 240 relative to the housing 212, and to also permit rotation of the housing 212 relative to the plunger 240. Preferably, the shells 214, 216 comprise one or more coupling features for providing engagement therebetween, for example, to form the housing 212. According to one example form, the coupling features are in the form of female projection elements 225 formed in the first housing shell 214 and male projection elements 226 formed in the second housing shell 216. As depicted in FIGS. 19-20, the coupling elements 225, 226 are generally positioned along at least a majority of the length of the housing (near the outer periphery thereof), and provide a snap fit engagement together, for example, to provide a generally elongate, cylindrical housing member 212. One of ordinary skill in the art will appreciate that the housing shells 214, 216 can couple together in a plurality of different formats and can comprise a plurality of different engagement features. Alternatively, the housing 212 is generally formed from one integrally formed, unitary member, for example, rather than two separate half-shell pieces. In further alterative embodiments, the outer housing shells are generally hingedly connected together, for example, such that the shells are capable of pivoting relative to each other between an open configuration and a closed, snapped-together configuration.

Figure 16:
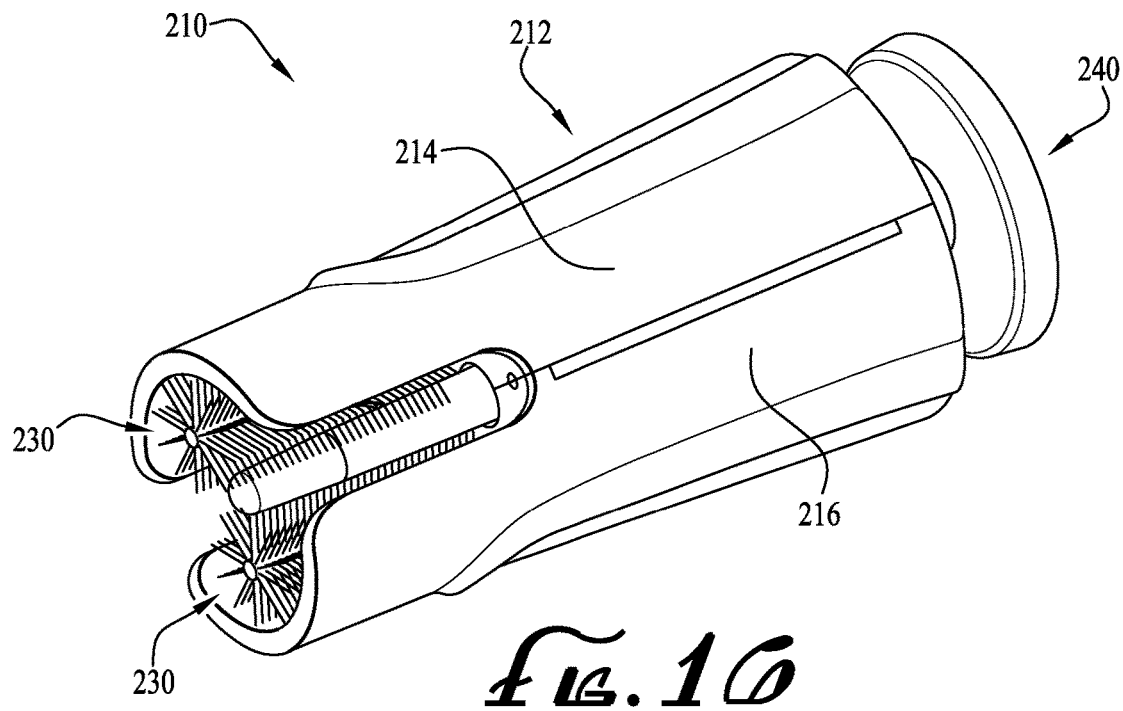
FIG. 16 shows a front perspective view of a cleaning device according to another example embodiment of the present invention, showing the plunger thereof in a retracted state.
Figure 17:
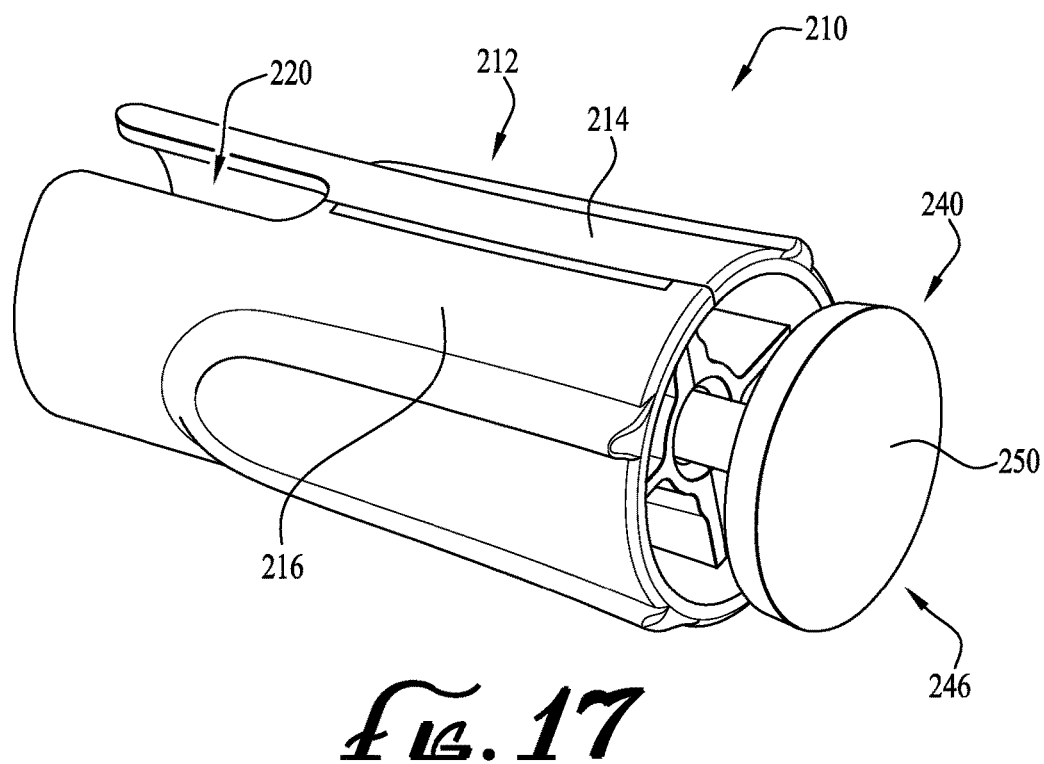
FIG. 17 shows a rear perspective view of the cleaning device of FIG. 16.
Figure 18:
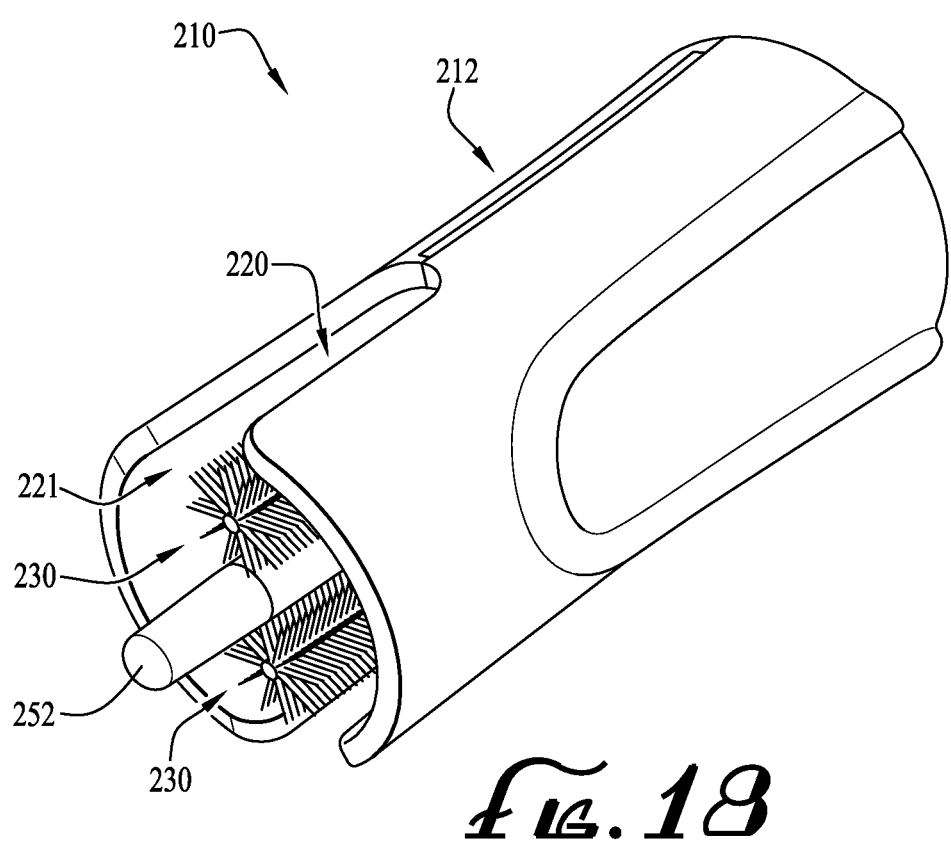
FIG. 18 shows a front perspective view of the cleaning device of FIG. 16, showing the plunger in the extended state.
Figure 21:
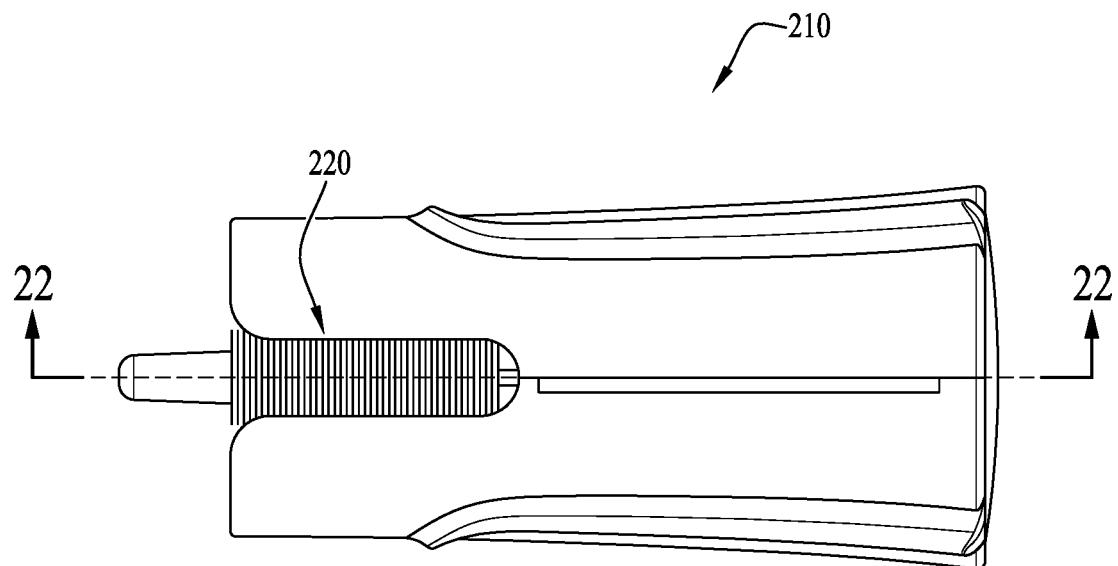
FIG. 21 shows a side view of the cleaning device of FIG. 18.
Figure 22:
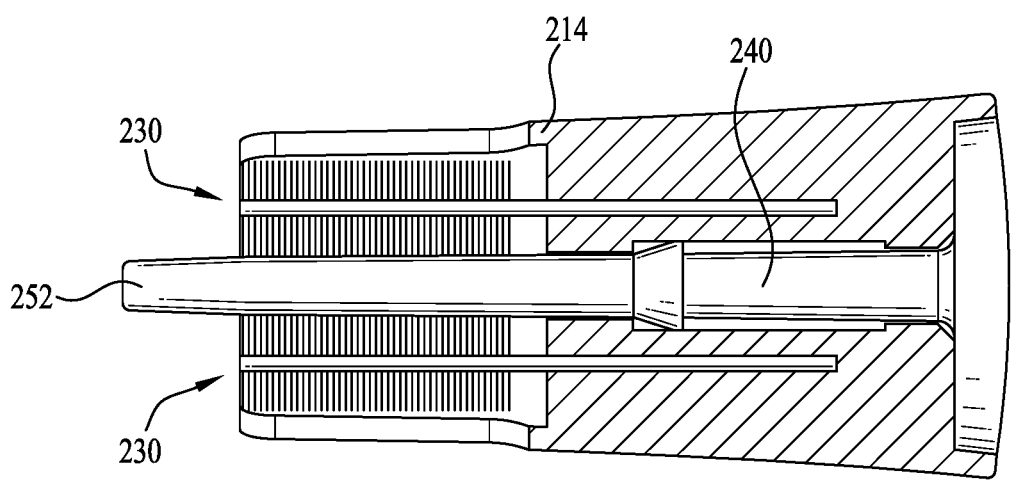
FIG. 22 shows a cross sectional view of the cleaning device of FIG. 21 taken along line 22-22.
Figure 23:
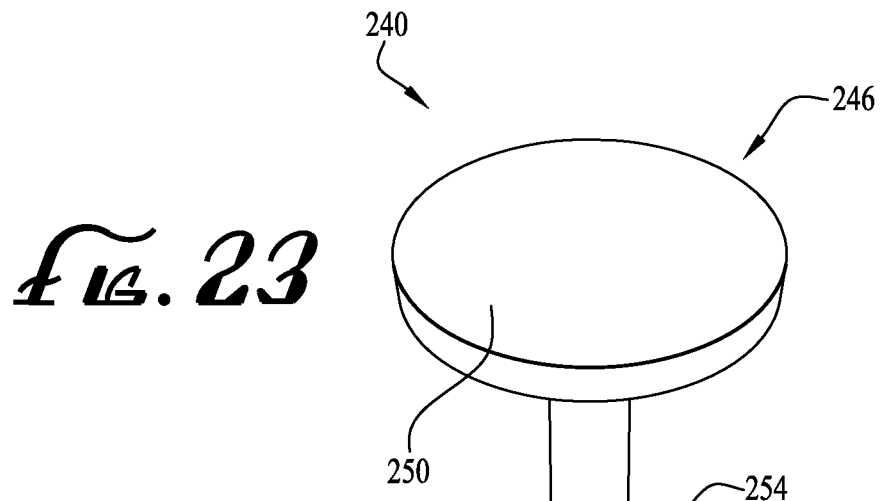
FIG. 23 shows a perspective view of the plunger of the cleaning device of FIG. 16.

As depicted in FIGS. 16-17, the plug 252 of the plunger 240 is generally in a retracted state within a portion of the housing and generally adjacent the flanges 224. In the retracted state, the plug 252 is generally intended to be engaged with the lumen of the connector such that the brushes 230 (generally laterally offset or spaced outwardly relative to the plug 252) can fully extend between the stem and the outer housing of the connector. As depicted in FIGS. 18 and 21-22, the plunger 240 is in the extended state wherein the plug 252 extends beyond the ends of the flanges 224. Generally described, the actuating portion, gripping pad or end portion 246 (comprising the flange 250) is generally fitted within the recessed area of the first end of the housing 212. Generally, when the cleaning device is not in use, the plug 252 remains in the extended state—projecting outwardly from the second end of the housing 212 beyond the flanges 224. In example forms, the flanges 224 are sized and shaped such that generally elongate, diametrically opposed channels 220 are defined along a portion of the housing, for example, generally starting at the second end of the housing 212 and extending towards the first end. In example forms, the channels provide access to the orifice 221 of the housing 212, for example, where the brushes 230 are positioned. As will be described below, the channels preferably provide for the application of a cleaning agent to the brushes 230 when the plug 252 is engaged with the lumen of the connector.

The plunger 240 generally comprises the end portion 246 having the flange 250 and a plug 252 at an end generally opposite the end portion 246 for engaging the lumen. The retaining feature 254 is generally positioned on a portion of the plunger 240 between the ends. Generally, the retention feature 254 is an outwardly-extending, skirt-like projection, which is preferably sized and shaped to movably mount within the central channel 222 of the housing 212. Preferably, the retention feature 254 is sized and shaped such that the plunger 240 is capable of translational and rotational movement relative to the housing 212, for example, to allow the housing 212 and brushes fixed relative to the housing 212 to move along the plunger rod once the plug 252 is engaged with the lumen of the connector. However, the retention feature 254 prevents the plunger 240 from becoming disengaged from the housing 212.

In example forms, each brush 230 generally comprises an elongate rod 232, whereby at least a portion of the rod 232 comprises a circular array of bristles 234 extending therefrom. According to example forms, the brush 230 comprises a circular array of about nine (9) linear arrays of bristles 234. According to one form, the length of each linear array of bristles 234 is generally between about 4-25 millimeters, for example between about 8-20 millimeters, and in a particular example about 14 millimeters. The entire length of the brush 230 is generally between about 10-50 millimeters, for example between about 20-40 millimeters, and in a particular example about 30.8 millimeters. According to example forms, the length of each bristle 234 is generally between about 1-5 millimeters, for example between about 2-4 millimeters, and in a particular example about 2.35 millimeters. According to example forms, the bristles 234 may be formed from any desired material. According to one example form, the bristles 234 are formed from a nylon filament, for example, DuPont Tynex® 612 nylon filament.

In use, the cleaning device 210 is provided for cleaning and disinfecting the area of the connector between the stem and outer housing portion. With the plunger in the extended state, the plug 252 is engaged with the lumen of the connector, and then the housing (and brushes 230 affixed thereto) are permitted to move along the length of the plunger 240 such that the bristles 234 extend within the connector between the stem and outer housing thereof. This causes the plunger 240 to be moved to the retracted state wherein the plug 252 is generally recessed within housing 212 near the second end (see FIGS. 16-17). In example forms, the flanges 224 of the housing are generally sized and shaped to permit the outer housing of the connector to be fitted therein, and wherein the brushes 230 (generally laterally offset from the flanges 224 and plug 252) are appropriately positioned to fit between the stem and an internal surface or wall of the outer housing of the connector. The housing 212 is then rotated around the plunger 240 (with the plug 252 engaged with the lumen) to clean and disinfect the connector. Once the cleaning and disinfecting of the connector has been performed, the user can disengage the cleaning device 210 from the connector by grasping the housing 212 and pulling away from the connector. Optionally, once the plug 252 of the plunger 240 is engaged with the lumen, and prior to the housing and brushes moving along the plunger 240 to clean and disinfect the connector, a cleaning agent can be applied to the bristles 234 of the brushes 230 through the channels 220. Thus, the cleaning device is configured such that a cleaning agent can be applied to the brushes 230 while in the connected state with the lumen of the stem.

In alternate embodiments, one, two, or more brushes can be mounted to the housing 212. Furthermore, the length of the brushes 230 and the bristles 234 may be longer or shorter in alternate embodiments. According to some example forms, multiple brushes having different brush lengths and bristle lengths may be provided for interchangeable or replaceable installation in the housing 212. Further optionally, the brushes may be mounted to the housing 212 by various different coupling means. For example, the brushes may be integrally formed with the housing 212 or formed with the housing 212 (or shells thereof) during the molding process, for example, by over molding.

Figure 25A:
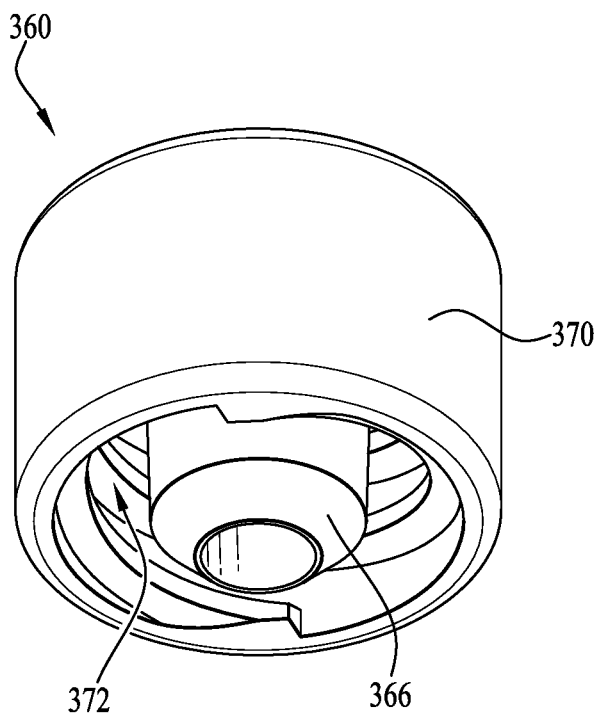
FIGS. 25A-26 show further examples of connectors or couplings to which the cleaning swab assemblies and methods of the present invention may be applied.
Figure 25B:
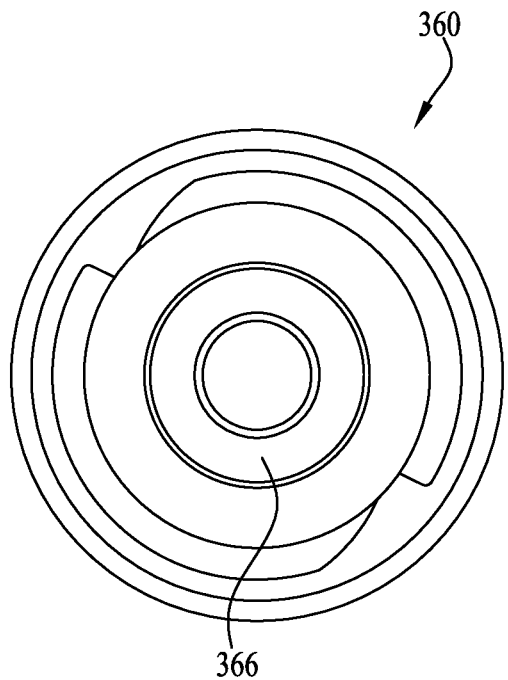
Figure 26:
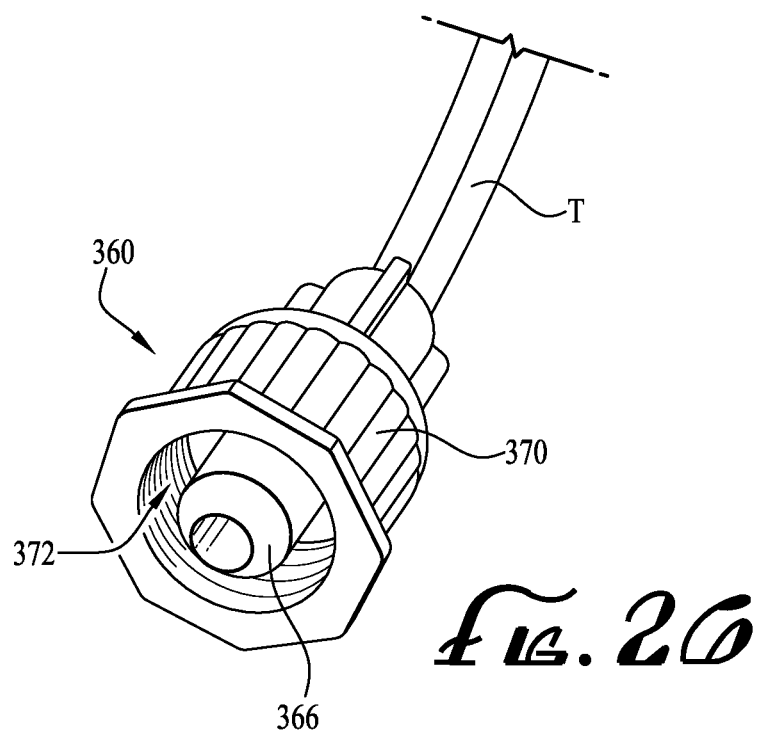

FIGS. 25A-26 show further details of a connector 360 according to example embodiments to which the cleaning swab devices (including brushes) and methods of the present invention may be applied, as described above. In example forms, the connector 360 is generally in the form of a male ENFit connector according to ISO 80369 standards, which comprises a stem 366 (comprising a lumen extending therethrough), an outer housing 370, and threads 372 formed on an internal portion of the outer housing 370. Generally, a tube T is coupled to a rear end portion thereof (and in communication with the lumen of the stem 366), which provides a conduit or path through which the feeding fluids flow. According to example forms, the connector 360 may be generally sized and shaped similarly to the connector 60 as described above. In one example embodiment, a swab 20 as shown above is used with or without a plunger 40 in similar fashion to the above described methods to clean the connector 360. According to another example form, a swab 20 without the elongate channel 32 (see dashed lines of FIG. 2 depicting the end of the tube 22 without the elongate channel 32) can be used with the connectors 60, 160, 360 to clean and disinfect the same, particularly when the connector does not include drainage or vent openings.

According to another example embodiment, the present invention relates to a method of cleaning and/or disinfecting a connector. As described above, the connector comprises a stem having a lumen extending therethrough, an outer housing, and threads positioned on an internal portion of the outer housing. The method comprises providing a cleaning device comprising a generally elongate cylindrical swab member comprising a first end and a second end, the first end generally opposite the second end, and an opening defined within the cylindrical member and extending from the first end to the second end; engaging an end of the swab with the connector, the end of the swab generally being positioned between the stem and the threads of the connector; translating and/or rotating the swab relative to the connector while the end of the swab is engaged with the connector; and disengaging the swab from the connector.

While the invention has been described with reference to preferred and example embodiments, it will be understood by those skilled in the art that a variety of modifications, additions and deletions are within the scope of the invention, as defined by the following claims.

What is claimed is:

1. A cleaning device for cleaning a connector, the connector comprising a stem and a lumen extending therethrough, the cleaning device comprising:
a handle defining a longitudinal central axis;
at least one brush mounted to the handle; and
a plunger coupled to the handle and generally extending along the longitudinal central axis, the plunger defining a first end and second end, the plunger comprising an actuating end at the first end such that the plunger can move along the longitudinal central axis.

2. The cleaning device of claim 1, wherein the at least one brush is positioned generally parallel to and laterally offset from the longitudinal central axis.

3. The cleaning device of claim 1, wherein the second end of the plunger is configured for projecting beyond an end of the handle for engagement with the stem of the connector.

4. The cleaning device of claim 3, wherein the plunger is configured for sealing engagement with the lumen of the stem.

5. The cleaning device of claim 1, wherein the connector further comprises an outer housing surrounding the stem and a space defined between the stem and outer housing, and wherein with the plunger sealingly engaged with the lumen the at least one brush can occupy at least a portion of the space to clean the space.

6. The cleaning device of claim 1, wherein the plunger is sized and shaped for sealing engagement with a lumen of an ISO 80369-3 formatted connector.

7. The cleaning device of claim 6, wherein the ISO 80369-3 formatted connector comprises a male ENFit connector.

8. The cleaning device of claim 1, further comprising at least two brushes mounted to the handle.

9. The cleaning device of claim 1, wherein the at least one brush and plunger are mounted to the handle to extend in a generally similar direction.

10. The cleaning device of claim 9, wherein the second end of the plunger is configured for extending at least partially beyond an end of the at least one brush.

11. A cleaning device for cleaning and/or disinfecting a connector, the connector comprising a stem having a lumen extending therethrough, an outer housing and threads positioned on an internal portion of the outer housing, the cleaning device comprising:
a generally elongate handle extending from a first end to a second end along a longitudinal axis;
a plunger extending along the longitudinal axis and defining a first end and second end, the plunger comprising an actuating end at the first end such that the plunger can move along the longitudinal central axis; and at least one brush mounted to the elongate handle, wherein the at least one brush can be inserted between the stem and the threads of the outer housing to clean the connector.

12. The cleaning device of claim 11, wherein when the at least one brush is inserted between the stem and the threads, the plunger sealingly engages with the lumen.

13. The cleaning device of claim 11, wherein the second end of the plunger is configured for extending at least partially beyond an end of the at least one brush.

14. The cleaning device of claim 11, wherein the connector comprises an ISO 80369-3 formatted connector.

15. The cleaning device of claim 14, wherein the ISO 80369-3 formatted connector comprises a male ENFit connector.

16. The cleaning device of claim 11, further comprising at least two brushes mounted to the handle.

17. The cleaning device of claim 11, wherein the at least one brush and plunger are mounted to the handle to extend in a generally similar direction.

18. A cleaning device for cleaning a connector, the connector comprising a stem having a lumen extending therethrough, the cleaning device comprising:
  a handle configured to be gripped by a user for application of the cleaning device into operative engagement with the connector, the handle defining a longitudinal central axis;
  a plunger coupled with the handle and configured for engagement with the lumen of the connector when the cleaning device is applied into operative engagement with the connector, the plunger defining a first end and second end, the plunger comprising an actuating end at the first end such that the plunger can move along the longitudinal central axis; and
  at least one brush coupled with the handle and laterally offset from the plunger, whereby the brush engages externally around the stem when the cleaning device is applied into operative engagement with the connector.

19. The cleaning device of claim 18, wherein the plunger is sized and shaped for sealing engagement with a lumen of an ISO 80369-3 formatted connector.

20. The cleaning device of claim 19, wherein the ISO 80369-3 formatted connector comprises a male ENFit connector.

21. The cleaning device of claim 18, wherein the second end of the plunger is configured for extending at least partially beyond an end of the at least one brush.

22. The cleaning device of claim 18, wherein the at least one brush and plunger are coupled to the handle such that they extend in a generally similar direction.

23. The cleaning device of claim 18, further comprising at least two brushes mounted to the handle.

* * * * *